US012648927B2

(12) United States Patent
Yee et al.

(10) Patent No.: US 12,648,927 B2
(45) Date of Patent: Jun. 9, 2026

(54) COMPOSITIONS AND METHODS OF ENHANCING IMMUNOTHERAPIES

(71) Applicant: Cha Therapeutics, Inc., Brookline, MA (US)

(72) Inventors: Amy Yee, Brookline, MA (US); Eric Paulson, Brookline, MA (US)

(73) Assignee: Cha Therapeutics, Inc., Brookline, MA (US)

( * ) Notice: Subject to any disclaimer, the term of this patent is extended or adjusted under 35 U.S.C. 154(b) by 884 days.

(21) Appl. No.: 17/293,648

(22) PCT Filed: Nov. 13, 2019

(86) PCT No.: PCT/US2019/061145
§ 371 (c)(1),
(2) Date: May 13, 2021

(87) PCT Pub. No.: WO2020/102325
PCT Pub. Date: May 22, 2020

(65) Prior Publication Data
US 2022/0008383 A1    Jan. 13, 2022

Related U.S. Application Data

(60) Provisional application No. 62/760,153, filed on Nov. 13, 2018.

(51) Int. Cl.
*A61K 31/353*        (2006.01)
*A61K 31/7068*      (2006.01)
(Continued)

(52) U.S. Cl.
CPC ........ *A61K 31/353* (2013.01); *A61K 31/7068* (2013.01); *A61K 40/11* (2025.01);
(Continued)

(58) Field of Classification Search
CPC .... A61K 31/52; A61K 39/3955; A61K 45/06; A61K 31/353; A61K 31/7068;
(Continued)

(56) References Cited

U.S. PATENT DOCUMENTS 3,870,790 A      3/1975  Lowey et al.
4,226,859 A    10/1980  Stach
(Continued)

FOREIGN PATENT DOCUMENTS

WO      WO-2011017096 A2 *   2/2011    ........... A61K 31/196
WO      WO-2011156119 A1 *  12/2011    ............. A61K 31/16
(Continued)

OTHER PUBLICATIONS

Nanda (Journal of Clinical Oncology vol. 34 pp. 2460-2470 published 2016). (Year: 2016).*
(Continued)

*Primary Examiner* — George W Kosturko
(74) *Attorney, Agent, or Firm* — WILSON SONSINI GOODRICH & ROSATI

(57) ABSTRACT

The present invention relates to compositions and methods of treating a subject having cancer by stimulating the subject's immune system and/or enhancing immunotherapies. Specifically, the present invention relates to methods of treating a subject by administering (1) a catechin ester or a derivative or metabolite thereof (e.g., EGCG) and (2) a nucleoside analogue (e.g., DAC), in combination with a checkpoint inhibitor or T-cell therapy.

20 Claims, 33 Drawing Sheets

Saline

EGCG/DAC

(51) Int. Cl.
  *A61K 40/11* (2025.01)
  *A61K 40/42* (2025.01)
  *C07K 16/28* (2006.01)
(52) U.S. Cl.
  CPC ...... *A61K 40/4211* (2025.01); *A61K 40/4268* (2025.01); *A61K 40/4269* (2025.01); *C07K 16/2818* (2013.01); *C07K 16/2827* (2013.01); *A61K 2239/49* (2023.05)
(58) Field of Classification Search
  CPC .... A61K 31/7072; A61K 40/11; A61K 40/42; A61P 35/00
  See application file for complete search history.

(56) References Cited

U.S. PATENT DOCUMENTS

| | | | |
|---|---|---|---|
| 4,369,172 A | 1/1983 | Schor et al. | |
| 4,842,866 A | 6/1989 | Horder et al. | |
| 5,217,720 A | 6/1993 | Sekigawa et al. | |
| 5,541,171 A | 7/1996 | Rhodes et al. | |
| 5,705,190 A | 1/1998 | Broad et al. | |
| 5,804,567 A * | 9/1998 | Cheng .................... | A61K 45/06 |
| | | | 549/399 |
| 5,858,358 A | 1/1999 | June et al. | |
| 5,883,223 A | 3/1999 | Gray | |
| 6,352,694 B1 | 3/2002 | June et al. | |
| 6,534,055 B1 | 3/2003 | June et al. | |
| 6,569,457 B2 | 5/2003 | Ullah et al. | |
| 6,638,534 B1 | 10/2003 | Ishibashi et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 7,572,631 B2 | 8/2009 | Berenson et al. | |
| 8,772,264 B2 * | 7/2014 | Kay ........................ | A61K 31/52 |
| | | | 514/47 |
| 2004/0110790 A1 * | 6/2004 | Zaveri ..................... | A61P 35/00 |
| | | | 549/406 |
| 2014/0274937 A1 | 9/2014 | Kay et al. | |
| 2016/0067336 A1 * | 3/2016 | Fandi ...................... | A61P 11/00 |
| | | | 424/143.1 |
| 2018/0186885 A1 | 7/2018 | Willert et al. | |
| 2019/0076397 A1 * | 3/2019 | Romero ............. | A61K 36/9066 |

FOREIGN PATENT DOCUMENTS

| | | |
|---|---|---|
| WO | WO-2018104909 A2 | 6/2018 |
| WO | WO-2018175179 A1 | 9/2018 |
| WO | WO-2020102325 A1 | 5/2020 |

OTHER PUBLICATIONS

Tyagi (Breast Cancer Research Treatment vol. 149 pp. 655-668 published 2015). (Year: 2015).*

Hong (Oncol. Lett. vol. 14 pp. 441-446 published May 2017). (Year: 2017).*

Wang (FASEBJ vol. 32 pp. 1537-1549 published online Mar. 2018) (Year: 2018).*

Tyagi (Breast Cancer Res Treat vol. 149 pp. 655-668 published 2015) (Year: 2015).*

Alamoudi, Mariam K. et al. CHA1: A New Combinatorial Therapy That Reciprocally Regulates Wnt and JAK/STAT/Interferon Signaling to Re-program Breast Tumors and the Tumor-Resident Landscape. BioRxiv:1-59 (2022).

Berge, et al., Selective expansion of a peripheral blood CD8+ memory T cell subset expressing both granzyme B and L-selectin during primary viral infection in renal allograft recipients, Transplant Proc., 30(8):3975-3977, (1998).

Berndsen, Robert H. et al. Epigenetic approach for angiostatic therapy: promising combinations for cancer treatment. Angiogenesis 20(2):245-267 (2017).

Dunn, Jennifer, and Sudha Rao. Epigenetics and immunotherapy: the current state of play. Molecular immunology 87:227-239 (2017).

EP20190885699.9 Extended European Search Report dated Jul. 12, 2022.

EP20190885699.9 Office Action dated Sep. 4, 2024.

Falahi, Fahimeh. et al. Current and upcoming approaches to exploit the reversibility of epigenetic mutations in breast cancer. Breast cancer research 16(4):412, 1-11 (2014).

Garland, et al., The use of Teflon cell culture bags to expand functionally active CD8q cytotoxic T lymphocytes, J. Immunol. Meth., 227(1-2):53-63, 1999.

Grupp, et al., Chimeric Antigen Receptor-Modified T Cells for Acute Lymphoid Leukemia, NEJM, 368(16):1509-1518, (2013).

Haanen, et al., Selective Expansion of Cross-reactive CD81 Memory T Cells by Viral Variants, J. Exp. Med., 190(9): 1319-1328, 1999.

International Preliminary Report on Patentability issued in PCT/US2019/061145, dated May 18, 2021.

International Search Report and Written Opinion issued in PCT/US2019/061145, mailed Mar. 30, 2020.

Kalos, et al., T Cells with Chimeric Antigen Receptors Have Potent Antitumor Effects and Can Establish Memory in Patients with Advanced Leukemia, Sci Transl Med., 3:95ra73, (2011).

Liu, et al., Synthesis of catechins via thiourea/auCl3-catalyzed cycloalkylation of aryl epoxides, J. Org. Chem., 73(12):4625-4629, (2008).

Pervin, Monira. et al. Function of Green Tea Catechins in the Brain: Epigallocatechin Gallate and its Metabolites. International journal of molecular sciences 20(15):3630, 1-12 (2019).

Porter, et al., Chimeric Antigen Receptor-Modified T Cells in Chronic Lymphoid Leukemia, NEJM, 365(8):725-733, (2011).

Sadelain, et al., The basic principle of chimeric antigen receptor (CAR) design, Cancer Discovery, 3(4):388-398, (2013).

Schantz, et al., Metabolism of green tea catechins by the human small intestine, Biotechnol. J., 5(10):1050-1059, (2010).

Stadlbauer, et al., A new synthetic strategy for catechin-class polyphenols: concise synthesis of (−)-epicatechin and its 3-O-gallate, Chem Commun., 48(67):8425-8427, (2012).

Takagaki, et al., Metabolism of (−)-epigallocatechin gallate by rat intestinal flora, J. Agric. Food Chem., 58(2):1313-1321, (2010).

Tyagi, Tulika. et al. Potentiation of growth inhibition and epigenetic modulation by combination of green tea polyphenol and 5-asa-2'-deoxycytidine in human breast cancer cells. Breast Cancer Research and Treatment 149:655-668 (2015).

Vuong, et al., Isolation of Green Tea Catechins and Their Utilization in the Food Industry, Food Reviews International, 27:227-247, (2011).

Wrangle, John. et al. Alterations of immune response of Non-Small Cell Lung Cancer with Azacytidine. Oncotarget 4(11):2067-2079 (2013).

Yee, et al. "Green Tea and Decitabine in the Treatment of Triple Negative Breast Cancer: Pre-clinical Studies on Alterations in Tumor Wnt Signaling and Immune Recognitions Properties" (Nov. 15, 2018) Tufts University Sackler School of Graduate Biomedical Sciences.

Kim, et al., Suppression of Wnt signaling by the green tea compound (−)-epigallocatechin 3-gallate (EGCG) in invasive breast cancer cells. Requirement of the transcriptional repressor HBP1, J Biol Chem., 281(16):10865-75, (2006).

Yee, et al., Epilepsy and the Wnt Signaling Pathway, grant No. W81XWH-10-1-0381, (2013 report).

Yee, et al., Epilepsy and the Wnt Signaling Pathway, grant No. W81XWH-10-1-0381, (2015 report).

Yee, et al., Triple negative breast cancer and metabolic regulation, grant No. W81XWH-13-1-0167, (2015 report).

(56) References Cited

OTHER PUBLICATIONS

Zhong, et al., Preparation of Epigallocatechin gallate Esters and Evaluation of Their Antioxidant, Antiviral, Anti-inflammatory and Anticancer Effects, Memorial University of Newfoundland, (2010).

Falkenstern, Lilia et al. A miniaturized mode-of-action profiling platform enables high throughput characterization of the molecular and cellular dynamics of EZH2 inhibition. Scientific Reports 14(1739):1-21 (2024).

Munna, Masudur Rahman et al. Unveiling promising phytocompounds from *Moringa oleifera* as dual inhibitors of EGFR$^{(T790M/C797S)}$ and VEGFR-2 in non-small cell lung cancer through in silico screening, ADMET, dynamics simulation, and DFT analysis. Journal of Genetic Engineering and Biotechnology 22(3):100406 (2024).

Nalla, Kirankumar et al. Epigallocatechin-3-gallate inhibit the protein arginine methyltransferase 5 and enhancer of Zeste homolog 2 in breast cancer both in vitro and in vivo. Archives of Biochemistry and Biophysics 763:110223 (2025) Epub 2024.

Wong, Iris L.K. et al. Synthesis and evaluation of stereoisomers of methylated catechin and epigallocatechin derivatives on modulating P-glycoprotein-mediated multidrug resistance in cancers. European Journal of Medicinal Chemistry 226:113795 (2021).

* cited by examiner

Saline                    EGCG/DAC

Saline

EGCG/DAC

Saline

EGCG/DAC

Ki67 staining

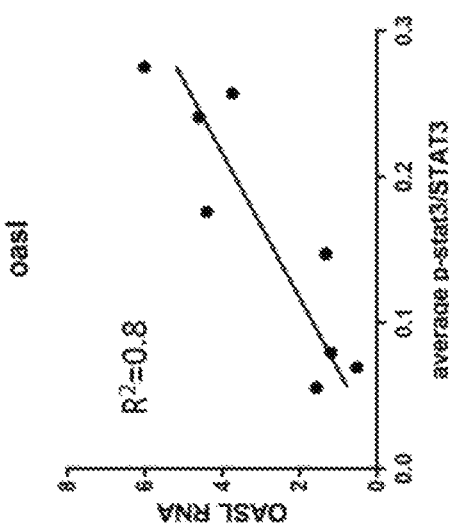
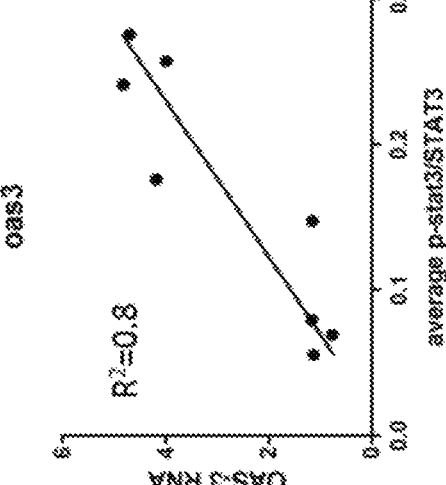
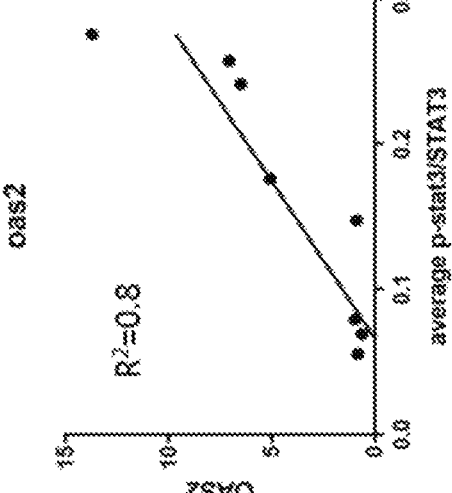
FIG. 20

PDL-1 Staining

PDL-1 Expression in Syngeneic Mouse Model

PD-1 and CTLA-4 Expression in
Syngeneic Mouse Model of TNBC

Syngeneic mouse model

LINE-1 Expression in Syngeneic model

Proposed Mechanisms of the Combination of EGCG and DAC

EGCG:

- Stabilize HBP1 mRNA
- Suppress Wnt signaling
- HBP1 inhibits DNMT1 promoter.

DAC:

- Inhibit DNMT1.
- sFRP1 and HBP1 are methylated in cancers
- sFRP1 and HBP1 are Wnt inhibitors.

Both EGCG/DAC cross the blood brain barrier.

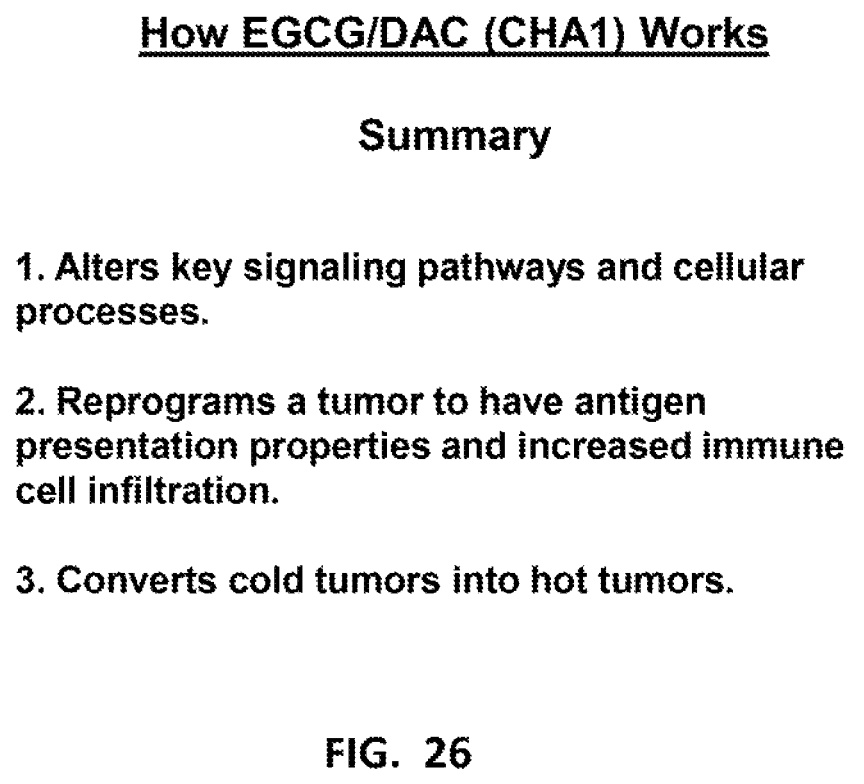

How EGCG/DAC (CHA1) Works

Summary

1. Alters key signaling pathways and cellular processes.

2. Reprograms a tumor to have antigen presentation properties and increased immune cell infiltration.

3. Converts cold tumors into hot tumors.

FIG. 26

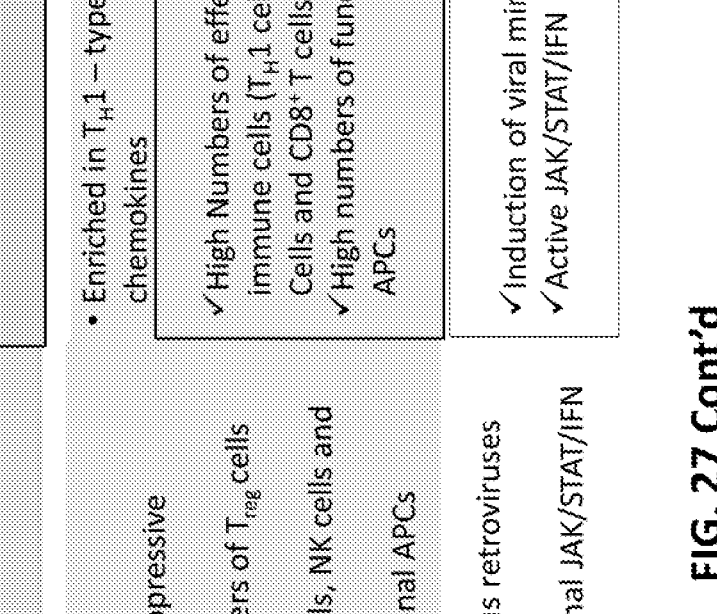

Biological characteristics

- Epigenetic silencing
- Active β-catenin signaling
- Mesenchymal-like cells
- Stem cell-like cells
- Less-differentiated cells ✓ Epigenetic reprogramming
✓ Suppressed β-catenin signaling
✓ Epithelial cells
✓ Highly differentiated cells
✓ Highly PDL1 expression

Immunological characteristics

- Enriched in immunosuppressive cytokines
- High numbers of T$_{reg}$ cells and MDSCs
- Few T$_H$1 cells, NK cells and CD8$^+$ cells
- Few functional APCs

• Enriched in T$_H$1 – type chemokines

✓ High Numbers of effector immune cells (T$_H$1 cells, NK Cells and CD8$^+$ T cells)
✓ High numbers of functional APCs

- Endogenous retroviruses silent
- Dysfunctional JAK/STAT/IFN

✓ Induction of viral mimicry
✓ Active JAK/STAT/IFN

Actions of EGCG/DAC (CHA1)

FIG. 27 Cont'd

Figure adapted from Nat Rev Immunol.
2017 Sep;17(9): 559-572

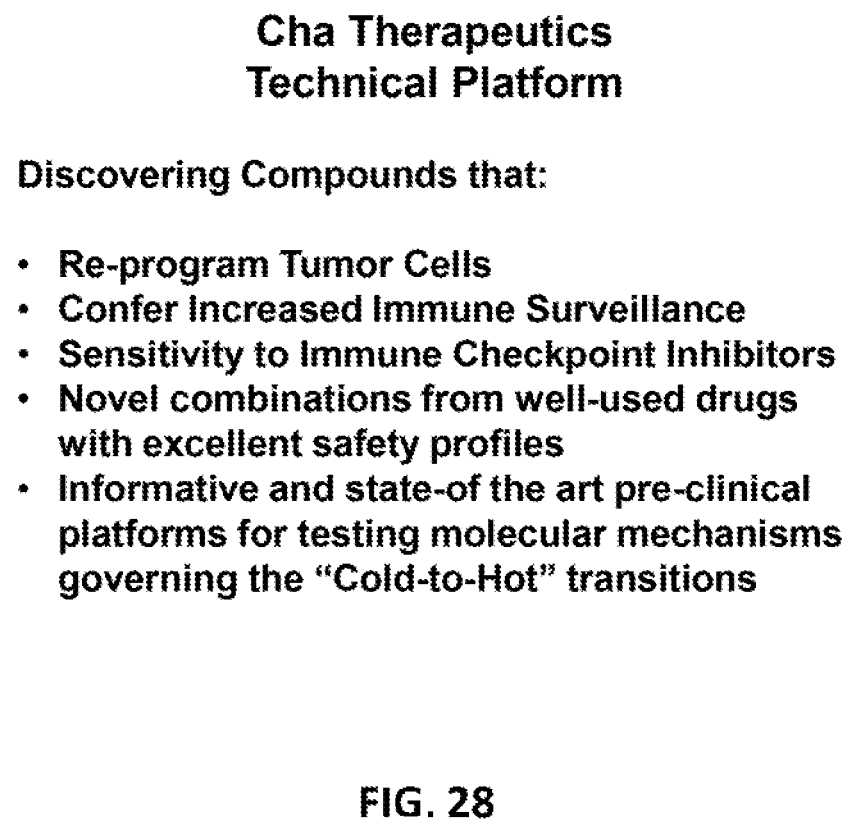

Cha Therapeutics
Technical Platform

Discovering Compounds that:

- Re-program Tumor Cells
- Confer Increased Immune Surveillance
- Sensitivity to Immune Checkpoint Inhibitors
- Novel combinations from well-used drugs with excellent safety profiles
- Informative and state-of the art pre-clinical platforms for testing molecular mechanisms governing the "Cold-to-Hot" transitions

FIG. 28

Cha Therapeutics Technical Platform - Identification of Cha1

Criteria for CHA1 (EGCG/DAC) and Like Compounds: "Cold" to "Hot" Transitions.

1. Inhibition of Wnt Signaling
2. Alteration of epithelial-mesenchymal Transitions
3. Re-expression of endogenous retrovirus expression
4. Activation of viral mimicry mechanisms
5. Activation of JAK/STAT signaling
6. Activation of Interferon Stimulated Gene Signature (e.g. PDL-1, MHCs, etc)
7. Re-expression of selected cancer testis antigens
8. Increased tumor immune cell infiltrations (e.g. CD8$^+$ T-cells).

FIG. 29A

Sample Experimental Analyses of Compound Functions

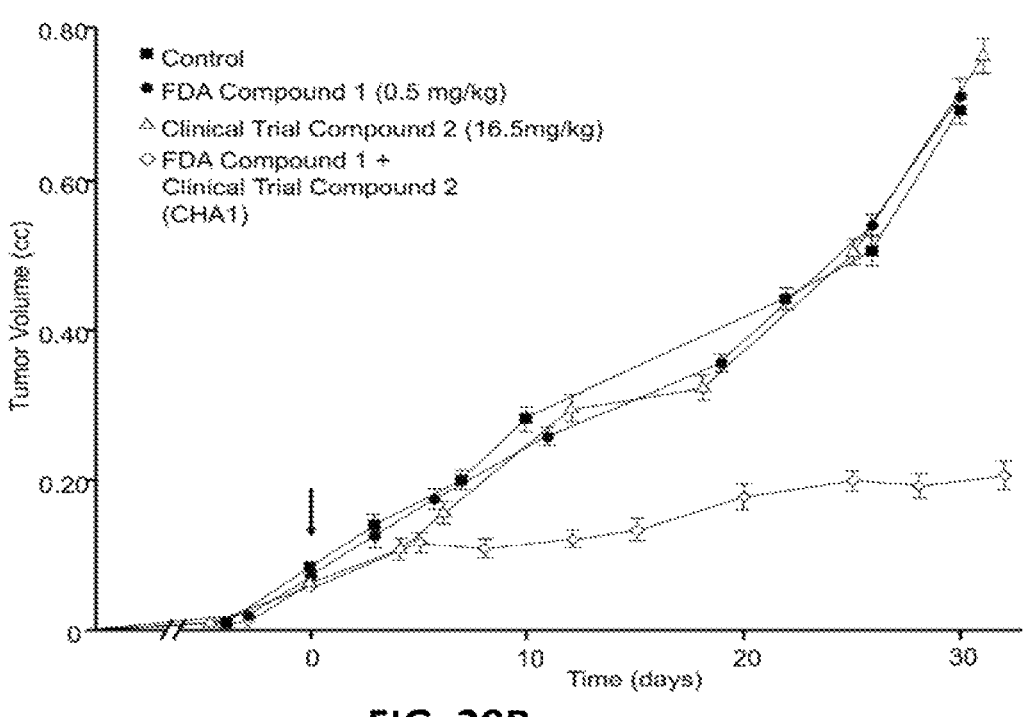

FIG. 29B

Sample Experimental Analyses of Compound Functions

Sample Experimental Analyses of Compound Functions

COMPOSITIONS AND METHODS OF ENHANCING IMMUNOTHERAPIES

CROSS-REFERENCE TO RELATED APPLICATION

This application is a § 371 U.S. National Stage Entry of International Application No. PCT/US2019/061145, filed Nov. 13, 2019, which claims the benefit of U.S. Application No. 62/760,153 filed Nov. 13, 2018, all of which are hereby incorporated by reference in their entirety.

GOVERNMENT SUPPORT

This invention was made with government support under Grant Number W81XWH-13-1-0167 awarded by the Department of Defense. The United States government has certain rights in the invention.

BACKGROUND

Cancer immunotherapy is the use of the immune system to treat cancer. Active immunotherapy (e.g., T-cell therapy) directs the immune system to attack tumor cells by targeting tumor antigens. Passive immunotherapies enhance existing anti-tumor responses and include the use of monoclonal antibodies (e.g., immune checkpoint inhibitors), lymphocytes and cytokines. However, not all cancers are susceptible to immune checkpoint inhibitors or T-cell therapies. An intense area of investigation is the identification of therapeutic strategies that may sensitize refractory tumors to immunotherapy. While several cancers have shown life-changing results with immune based therapies, the vast majority of cancers can be refractory to immune-based therapies by some known and to-be-discovered mechanisms.

Triple negative breast cancer (TNBC) represents 20-25% of sporadic breast cancers and is the most clinically challenging breast cancer subtype. TNBC has an exceptionally poor prognosis with high recurrence and metastases. TNBC lacks expression of the three key molecular parameters of breast cancer—ER, PR, and overexpressed Her2—and thus have no targeted treatment options. While classified pathologically by negative criteria, TNBC is also heterogeneous group of breast cancers, currently subclassified by anecdotal clinical experience. TNBC has significant mortality and currently represents an unmet medical need. Thus, there remains a need for drugs and methods that can enhance cancer immunotherapies, particularly against cancers like TNBC.

SUMMARY

The present invention relates to compositions and methods of treating a subject having cancer by stimulating the subject's immune system and/or enhancing immunotherapies. Specifically, the present invention relates to methods of treating a subject by administering (1) a catechin ester or a derivative or metabolite thereof (e.g., EGCG) and (2) a nucleoside analogue (e.g., DAC), in combination with a checkpoint inhibitor or T-cell therapy. In one aspect, provided herein is a method of treating a subject having cancer, the method comprises administering to the subject (1) a catechin ester or a derivative or metabolite thereof, (2) a nucleoside analogue, and (3) a checkpoint inhibitor, wherein a weight ratio of the catechin ester or a derivative or metabolite thereof to the nucleoside analogue is from about 4:1 to about 400:1. In one aspect, provided herein is a method of stimulating a subject's immune system against cancer cells, the method comprises administering to the subject (1) a catechin ester or a derivative or metabolite thereof, (2) a nucleoside analogue, and (3) a checkpoint inhibitor, wherein a weight ratio of the catechin ester or a derivative or metabolite thereof to the nucleoside analogue is from about 4:1 to about 400:1. In another aspect, provided herein is a method of treating a subject having cancer, the method comprises administering to the subject (1) a catechin ester or a derivative or metabolite thereof, (2) a nucleoside analogue, and (3) an effective amount of T cells that express at least one chimeric antigen receptor (CAR), wherein a weight ratio of the catechin ester or a derivative or metabolite thereof to the nucleoside analogue is from about 4:1 to about 400:1. In yet another aspect, provided herein is a method of stimulating a subject's immune system against cancer cells, the method comprises administering to the subject (1) a catechin ester or a derivative or metabolite thereof, (2) a nucleoside analogue, and (3) an effective amount of T cells that express at least one chimeric antigen receptor (CAR), wherein a weight ratio of the catechin ester or a derivative or metabolite thereof to the nucleoside analogue is from about 4:1 to about 400:1. In some embodiments, the nucleoside analogue is a deoxycytidine analogue, deoxyuridine analogue, or a thymidine or deoxythymidine analogue. In some embodiments, the nucleoside analogue is azacytidine or decitabine (DAC). In some embodiments, the nucleoside analogue is DAC. In some embodiments, the catechin ester or a derivative or metabolite thereof is an epigallocatechin or epicatechin ester. In some embodiments, the catechin ester or a derivative or metabolite thereof is epigallocatechin gallate (EGCG) or epicatechin gallate (ECG). In some embodiments, the catechin ester or a derivative or metabolite thereof is a catechin metabolite selected from 3'-O-methyl EGC; 4'-O-methyl EGC; 3'-O-methyl EC; 4'-O-methyl EC; 1-(3',4',5'-trihydroxyphenyl)-3-(2",4",6"-trihydroxyphenyl)propan-2-ol; and 1-(3',5'-dihydroxyphenyl)-3-(2",4",6"-trihydroxyphenyl)propan-2-ol. In some embodiments, the catechin ester is an EGCG/fatty acid or ECG/fatty acid monoester or polyester. In some embodiments, the cancer is a solid tumor. In some embodiments, the cancer has origins or metastases in breast, bone, lung, liver, brain, stomach, intestine, colorectal, prostate, ovarian, uterine, cervical, kidney, spine, smooth muscle, skeletal muscle, or any other human organ. In some embodiments, the cancer is a triple negative breast cancer. In some embodiments, the immune stimulation comprises reduction of Wnt signaling and proliferation. In some embodiments, the immune stimulation comprises attenuation of a Warburg-like metabolism. In some embodiments, the immune stimulation comprises activating antigen expression or presentation. In some embodiments, the immune stimulation comprises augmenting JAK/STAT signaling. In some embodiments, the immune stimulation comprises activating IFN signaling. In some embodiments, the checkpoint inhibitor is a PD-1 inhibitor, a PD-L1 inhibitor, or a CTLA-4 inhibitor. In some embodiments, the checkpoint inhibitor is an anti-PD-1 antibody, an anti-PD-L1 antibody, or an anti-CTLA-4 antibody. In some embodiments, the checkpoint inhibitor is Ipilimumab, Nivolumab, Pembrolizumab, Atezolizumab, Avelumab, or Durvalumab. In some embodiments, the (1) catechin ester or a derivative or metabolite thereof and the (2) nucleoside analogue are administered simultaneously. In some embodiments, the (1) catechin ester or a derivative or metabolite thereof and the (2) nucleoside analogue are administered on alternating days. In some embodiments, the (1) catechin ester or a derivative or metabolite thereof, the (2) nucleoside analogue, or both are administered over a period of at least 1 day, 2 days, 3 days, 4 days, 5 days, 6 days, 1 week, 2 weeks, 3 weeks, 4 weeks, 5 weeks, 10 weeks, 20 weeks, 40 weeks, 1 year, or 2 years. In some embodiments, the (1) catechin ester or a derivative or metabolite thereof, the (2) nucleoside analogue, or both are administered 1, 2, 3, 4, 5 or more times a day or 1, 2, 3, 4, 5, 6, 7 or more times a week. In some embodiments, the (1) catechin ester or a derivative or metabolite thereof, the (2) nucleoside analogue, and the checkpoint inhibitor are administered simultaneously. In some embodiments, the (1) catechin ester or a derivative or metabolite thereof, the (2) nucleoside analogue, and the checkpoint inhibitor are administered sequentially. In some embodiments, the (1) catechin ester or a derivative or metabolite thereof, the (2) nucleoside analogue, and the T lymphocyte cells are administered simultaneously. In some embodiments, the (1) catechin ester or a derivative or metabolite thereof, the (2) nucleoside analogue, and the T lymphocyte cells are administered sequentially. In some embodiments, the at least one chimeric antigen receptor (CAR) and/or the corresponding T-cells are directed to CD8, CD4, CD19, CD22, CD123, NY-ESO1, Mage-A3, MAGE A6, mucin1, cMET, TEM8, MART-1, gp100, CEA, hTERT, EGFR, mesothelin, HPV, EBV, MCC, B-catenin, CDK4, ERBB2IP, or a combination thereof. In some embodiments, the at least one chimeric antigen receptor (CAR) and/or the corresponding T-cells are directed to CD19, Mage-A3, MAGE A6, or NY-ESO1. In some embodiments, the catechin ester or a derivative or metabolite thereof is administered at least about 0.1 mg/kg, 0.5 mg/kg, 1 mg/kg, 2 mg/kg, 5 mg/kg, 10 mg/kg, 15 mg/kg, 20 mg/kg, 25 mg/kg, 30 mg/kg, 50 mg/kg, or 100 mg/kg per administration. In some embodiments, the catechin ester or a derivative or metabolite thereof is administered at most about 5 mg/kg, 10 mg/kg, 15 mg/kg, 20 mg/kg, 25 mg/kg, 30 mg/kg, 50 mg/kg, 100 mg/kg, or 1000 mg/kg per administration. In some embodiments, the nucleoside analogue is administered at least about 0.15 mg/m$^2$, 0.5 mg/m$^2$, 1 mg/m$^2$, 1.5 mg/m$^2$, 2 mg/m$^2$, 5 mg/m$^2$, 10 mg/m$^2$, 15 mg/m$^2$, 20 mg/m$^2$, 30 mg/m$^2$, 40 mg/m$^2$, 50 mg/m$^2$, or 100 mg/m$^2$ per administration. In some embodiments, the nucleoside analogue is administered at most about 2 mg/m$^2$, 10 mg/m$^2$, 15 mg/m$^2$, 20 mg/m$^2$, 30 mg/m$^2$, 40 mg/m$^2$, 50 mg/m$^2$, 100 mg/m$^2$, 200 mg/m$^2$, or 500 mg/m$^2$ per administration. In some embodiments, a weight ratio of the catechin ester or a derivative or metabolite thereof to the nucleoside analogue is from about 1:1 to about 100:1, from about 10:1 to about 90:1, from about 10:1 to about 80:1, from about 10:1 to about 70:1, from about 10:1 to about 60:1, from about 10:1 to about 50:1, from about 20:1 to about 40:1, or from about 25:1 to about 35:1. In some embodiments, the dose of the (1) catechin ester or a derivative or metabolite thereof, the (2) nucleoside analogue, or both are determined by an up-titration. In some embodiments, the (1) catechin ester or a derivative or metabolite thereof, the (2) nucleoside analogue, or both are administered orally, topically, parenterally, or by inhalation. In some embodiments, the (1) catechin ester or a derivative or metabolite thereof, the (2) nucleoside analogue, or both are administered orally or by injection. In some embodiments, the catechin ester or a derivative or metabolite thereof is administered orally. In some embodiments, the nucleoside analogue is administered intravenously or orally.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawing (also "figure" and "FIG." herein), of which:

FIG. 1A and FIG. 1B illustrate the effect of EGCG/DAC on tumor growth in a triple negative breast cancer (TNBC) human xenograft (immune compromised) mouse model.

FIG. 3A shows the top 20 signaling pathways by p-value affected by EGCG/DAC. FIG. 3B shows the same top 20 signaling pathways with the fractional activation or inhibition by EGCG/DAC. Dark grey and black arrows indicate activated immune function pathways, while light grey and white arrows indicate inhibited Wnt signaling pathway.

FIG. 5A illustrates a representative saline (control) tumor. FIG. 5B illustrates a representative EGCG/DAC treated tumor. FIG. 5C illustrates the quantification by percentage of 4 individual control and 4 individual treated tumors. * represents $p < 0.05$.

FIG. 6A illustrates a representative saline (control) tumor. FIG. 6B illustrates a representative EGCG/DAC treated tumor. FIG. 6C illustrates the quantification by percentage of 4 individual control and 4 individual treated tumors. * represents p<0.05.

FIG. 11A illustrates a representative saline (control) tumor and a representative EGCG/DAC treated tumor. FIG. 11B illustrates the quantification by percentage of 4 individual control and 4 individual treated tumors. * represents p<0.05.

FIG. 13A illustrates a representative saline (control) tumor and a representative EGCG/DAC treated tumor. FIG. 13B illustrates the quantification by percentage of 4 individual control and 4 individual treated tumors. * represents p<0.05.

FIG. 14A illustrates a representative saline (control) tumor and a representative EGCG/DAC treated tumor. FIG. 14B illustrates the quantification by percentage of 4 individual control and 4 individual treated tumors. * represents p<0.05.

FIG. 18 illustrates the fold change in mRNA level determined by qRT-PCR for IFN stimulated genes (ISGs) in a TNBC syngeneic (immune competent) mouse model. * represents p<0.05,  represents p<0.01, * represents p<0.005

FIG. 19 illustrates that EGCG/DAC induces apoptosis via perforin/granzyme pathway in a mouse model measuring PFR-1 mRNA using qRT-PCR. * represents p<0.05.

FIG. 20 illustrates a correlation between STAT3 phosphorylation and ISGs expression. STAT3 Y705 status as determined for each sample in FIG. 17A-FIG. 17B is represented on the X-axis, while ISG expression status as determined for each sample in FIG. 18 is represented on the Y-axis. Linear regression analysis was done (Prism 7.0) and $R^2 \geq 0.8$ indicate strong correlation.

FIG. 21A illustrates a representative saline (control) tumor and a representative EGCG/DAC treated tumor. FIG. 21B illustrates the quantification by percentage of 4 individual control and 4 individual treated tumors. * represents p<0.05. FIG. 21C illustrates the synergy of the compound combination for PDL-1 expression measured using qRT-PCR in the human MDA-MB-231 xenograft mouse model (immune incompetent). * represents p<0.05, ** represents p<0.005.

FIG. 23A illustrates the fold change in mRNA level from 4 individual control and 4 individual EGCG/DAC treated tumors of mouse endogenous retrovirus Erv3-1, determined by qRT-PCR, in a TNBC syngeneic (immune competent) mouse model. * represents p<0.05. FIG. 23B illustrates the fold change in mRNA level from 4 individual control and 4 individual EGCG/DAC treated tumors of the mouse LINE-1 ORF-1, determined by qRT-PCR, in a TNBC syngeneic (immune competent) mouse model. * represents p<0.05.

FIG. 24A shows western blot analysis for E-cad in 4 untreated mice and 4 EGCG/DAC treated mice. FIG. 24B shows a quantification graph combining data from two western blot each with 4 untreated and 4 treated samples. * represents p<0.05

FIG. 26 illustrates a summary of the outcomes of the EGCG/DAC combination (CHA1) in altering the fate of the tumor by: 1) Altering important signaling pathways such as Wnt, 2) reprograming the tumor to increase antigen presentation in immune cell infiltration and 3), changing the tumor from immunologically "cold" to having immunologically "hot" characteristics.

FIG. 28 illustrates a summary of the Cha Therapeutics scientific and technical platform, derived from the analysis of EGCG/DAC on TNBC tumors, for analysis of compounds capable of re-programing tumor cells to engage the immune system.

FIG. 29A illustrates the details of the Cha Therapeutics scientific and technical platform for evaluating candidate compounds that function in a manner similar to EGCG/DAC. The specific criteria are: 1) inhibition of Wnt signaling, 2) alteration of epithelial-mesenchymal transitions, 3)re-expression of endogenous retrovirus expression, 4) activation of viral mimicry mechanisms, 5) activation of JAK/STAT signaling, 6) activation of an interferon stimulated gene signature (e.g. PDL-1, MHCs, etc), 7) re-expression of selected cancer testis antigens (CTAs) and 8) increased tumor immune cell infiltration (e.g. CD8$^+$ T-cells); FIG. 29B illustrates sample experimental analyses of compound functions.

DETAILED DESCRIPTION

Figure 1A:
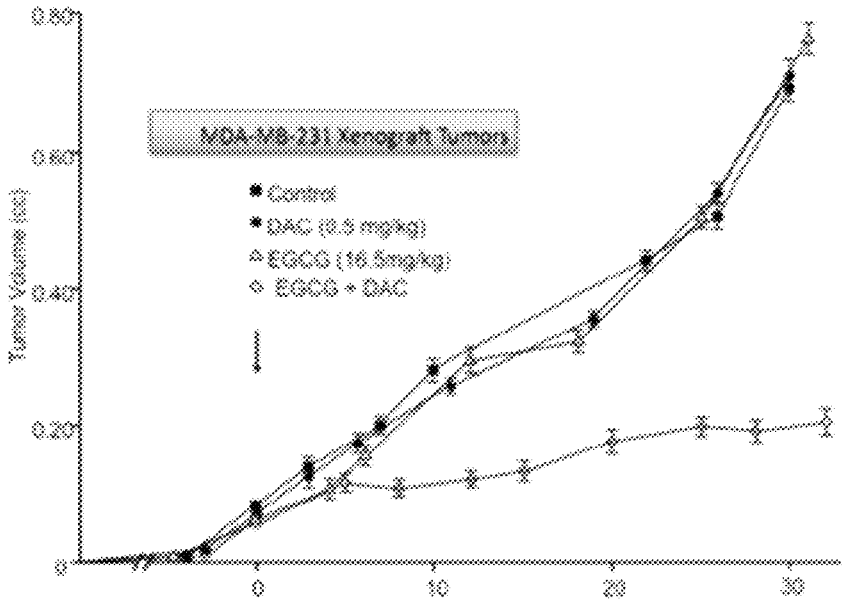
FIG. 1A illustrates the tumor volume growth for mice treated with the indicated therapies and FIG. 1B shows the bioluminescence imaging of EGCG and DAC treated xenograft mice.

The present invention relates to compositions and methods of treating a subject having cancer by enhancing immunotherapies. The present invention further relates to methods of treating a subject by administering (1) a catechin ester or a derivative or metabolite thereof (e.g., EGCG) and (2) a nucleoside analogue (e.g., DAC), in combination with a checkpoint inhibitor or T-cell therapy.

The following description and examples illustrate embodiments of the present disclosure in detail. It is to be understood that this present disclosure is not limited to the particular embodiments described herein and as such can vary. Those of skill in the art will recognize that there are numerous variations and modifications of this present disclosure, which are encompassed within its scope.

Although various features of the present disclosure may be described in the context of a single embodiment, the features may also be provided separately or in any suitable combination. Conversely, although the present disclosure may be described herein in the context of separate embodiments for clarity, the present disclosure may also be implemented in a single embodiment.

The section headings used herein are for organizational purposes only and are not to be construed as limiting the subject matter described.

All terms are intended to be understood as they would be understood by a person skilled in the art. Unless defined otherwise, all technical and scientific terms used herein have the same meaning as commonly understood by one of ordinary skill in the art to which the disclosure pertains.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

I. Definitions

The terminology used herein is for the purpose of describing particular cases only and is not intended to be limiting. In this application, the use of the singular includes the plural unless specifically stated otherwise. As used herein, the singular forms "a", "an" and "the" are intended to include the plural forms as well, unless the context clearly indicates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value should be assumed.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures. To facilitate an understanding of the present disclosure, a number of terms and phrases are defined below.

The term "pharmaceutically acceptable" refers to approved or approvable by a regulatory agency of the Federal or a state government or listed in the U.S. Pharmacopeia or other generally recognized pharmacopeia for use in animals, including humans.

A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

A "pharmaceutically acceptable salt" suitable for the combination therapy may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethyl sulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, $HOOC$—$(CH_2)n$-$COOH$ where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts include those listed by Remington's Pharmaceutical Sciences, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

As used herein, the terms "prevent," "preventing," "prevention," "prophylactic treatment," and the like, refer to reducing the probability of developing a disease or condition in a subject, who does not have, but is at risk of or susceptible to developing a disease or condition.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

A "receptor" is to be understood as meaning a biological molecule or a molecule grouping capable of binding a ligand. A receptor may serve, to transmit information in a cell, a cell formation or an organism. The receptor comprises at least one receptor unit and frequently contains two or more receptor units, where each receptor unit may consist of a protein molecule, in particular a glycoprotein molecule. The receptor has a structure that complements the structure of a ligand and may complex the ligand as a binding partner. Signaling information may be transmitted by conformational changes of the receptor following binding with the ligand on the surface of a cell.

The term "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

The terms "treat," "treated," "treating," "treatment," and the like are meant to refer to reducing or ameliorating a disorder and/or symptoms associated therewith (e.g., a neoplasia or tumor). "Treating" may refer to administration of the combination therapy to a subject after the onset, or suspected onset, of a cancer. "Treating" includes the concepts of "alleviating", which refers to lessening the frequency of occurrence or recurrence, or the severity, of any symptoms or other ill effects related to a cancer and/or the side effects associated with cancer therapy. The term "treating" also encompasses the concept of "managing" which refers to reducing the severity of a particular disease or disorder in a patient or delaying its recurrence, e.g., lengthening the period of remission in a patient who had suffered from the disease. The term "treating" further encompasses the concept of "prevent," "preventing," "prevention," and "prophylactic treatment" as previously stated. It is appreciated that, although not precluded, treating a disorder or condition does not require that the disorder, condition, or symptoms associated therewith be completely eliminated.

The term "therapeutic effect" refers to some extent of relief of one or more of the symptoms of a disorder (e.g., a neoplasia or tumor) or its associated pathology. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. The amount of the compound combination of (a) a catechin ester or a derivative thereof (e.g., epigallocatechin gallate (EGCG)) and (b) a nucleoside analogue (e.g., decitabine (DAC)) may be referred to as a therapeutically effective amount if it is effective in enhancing cancer immunotherapy, stimulating immune system or sensitizing refractory tumors. "Therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required. For example, the physician or veterinarian could start doses of the compounds of the invention employed in a pharmaceutical composition at levels lower than that required in order to achieve the desired therapeutic effect and gradually increase the dosage until the desired effect is achieved.

II. Technical Description

Described herein is a discovery of a compound combination to improve cancer treatment by potentially conferring susceptibility to immune system-based therapies including immune checkpoint inhibitors and CAR-T therapies. The key aspects of the mechanism include the efficacy in modulating two signaling pathways that are both important to dictating the tumor response and interactions with the immune system. Unexpectedly, one aspect of the mechanism is the induction of antigen-presentation genes and machinery that are normally expressed in antigen-presentation cells and not usually epithelial tumor cells. In our experimental systems, it is the effects of combining (a) a catechin ester or a derivative thereof (e.g., epigallocatechin gallate (EGCG)) with (b) a nucleoside analogue (e.g., decitabine (DAC)) that endow the tumor with unusual visibility to the immune system and markedly diminish tumor growth. The alteration of the intrinsic tumor properties with respect to immune system visibility and reaction provide an ideal scenario to endow a susceptibility to immune based therapies on otherwise "cold" tumors that have escaped immune cell infiltration and destruction. The application of the herein described combination should alter tumor properties and confer susceptibility to immune-based treatments.

The discovery of the actions and mechanisms of the herein described combination (as illustrated in FIG. 24) occurred unexpectedly and could not have been predicted. We used systematically and well-designed studies to dissect the mechanisms by which the combination appeared to suppress growth of primary tumors and the distant metastases in a preclinical model. While we reasoned that a combination of (a) a catechin ester or a derivative thereof (e.g., EGCG) with (b) a nucleoside analogue (e.g., DAC) might suppress Wnt signaling, the unbiased transcriptomic analysis of treated tumors, followed by multiple additional experiments, revealed the tumor had been dramatically re-programed in multiple ways, resulting in the hallmarks of increased visibility to the immune system. This reprogramming altered both the biological and immunological characteristics of the tumor, revealing a platform for analysis of any compound that can act in the same manner.

1. Wnt signaling is inhibited.
2. Mesenchymal character of the tumor is re-programmed back to a epithelial-like state.
3. Expression of endogenous retroviruses are actived.
4. The viral mimicry response is induced.
5. Interferon-like JAK/STAT signaling is induced.
6. An interferon-stimulated gene signature is elicited, including increased expression of MHC proteins and PDL1.
7. Cancer Testis Antigens are rexpressed, a signature of increased immunogenicity
8. Increased immunogenicity is observed, including tumor infiltration of T-cells and macrophage.

One cancer testis antigen (NYESO1) is induced greater than 600-fold on the gene level. NYESO1 is used in screening patient efficacy for the FDA-approved CAR-T therapy. CAR-T is currently approved for hematological malignancies, but the availability of the compound combination identified here might also be used in the CAR-T setting.

This compound combination addresses the known problem of aggressive breast cancer growth and the immune-privilege nature of all cancers. In the current climate of cancer treatments, there have been successes as well as lack of responses with immune checkpoint inhibitors/immunotherapy. Increased T-cell infiltration is a primary observation for tumors that are susceptible to immune system based therapies such as checkpoint inhibitors.

Similarly, the level of PDL-1 expression is an indicator of the success of anti-PDL-1 immunotherapy (i.e. Keytruda, Merck). Keytruda is used either in combination with standard-of-care chemotherapy, or as monotherapy for a number of cancers including melanoma and lung cancer. By increasing PDL-1 expression 3-6 fold, this compound combination is likely to increase the efficacy of immunotherapies such as Keytruda.

Many cancers, breast or otherwise, are not susceptible to immune checkpoint inhibitors. An intense area of investigation is the identification of therapeutic strategies that may sensitize refractory tumors to immunotherapy. While several cancers have shown life-changing results with immune based therapies, the vast majority of cancers appear refractory to immune-based therapies by some known and to-be-discovered mechanisms.

The action of the combination of (a) a catechin ester or a derivative thereof (e.g., EGCG) and (b) a nucleoside analogue (e.g., DAC) on breast tumors may increase immunogenicity of the primary tumors and susceptibility to immune based cancer therapies. Prior studies in melanomas (non-breast tumors) have reported that elevated Wnt signaling and diminished interferon signaling biochemically renders tumors resistant to immune checkpoint inhibitors. Unexpected results from the treated tumors revealed global alterations in antigen presentation and other properties normally attributed to immune system function in the (unrelated) epithelial triple negative breast tumors (TNBC). The net consequences are an increase visibility to the immune system in a viral "mimicry-like" mechanism.

By initially using human xenografts in an immune compromised mouse model, we were able to delineate the effects of the combination on human TNBC tumors. Remarkably, antigen-presenting properties of the breast triple-negative tumors were dramatically induced. Thus, human genes that are normally induced in T-cells were now induced in the treated tumors. Similarly, human genes consistent with natural killer cell-mediated apoptosis were also induced in the tumor. Because we were investigating human genes, such effect could only be attributable to the human tumor itself.

Such molecular changes should promote an increased interaction with T-cells, when there is a functional immune system. Using a mouse triple-negative breast xenograft in a mouse with a competent immune system, there was increased infiltration of both macrophages and cytotoxic T-cells. The full breadth of immune system recruitment is under investigation.

The dramatic alteration of the tumor properties could not have been predicted a priori from any of our objectively configured studies. The unbiased bioinformatics/RNA-seq analysis of the human xenograft tumors in the immune-compromised mouse revealed the gene expression changes specifying increase antigen presentation properties in the tumor. Further, the combination of EGCG and DAC often acted in a synergistic manner, amplifying the effect of either compound individually. These changes were mirrored in the syngeneic mouse model, although because of the fully mouse system, it is not possible to distinguish gene expression changes emanating from the tumor or immune cells.

The combination of (a) a catechin ester or a derivative thereof (e.g., EGCG) and (b) a nucleoside analogue (e.g., DAC) represent two types of compounds that some of which are already in clinical trials or approved by the FDA for treatment of hematologic malignancies, respectively. The safety profile and known side effects of both types of compounds are generally well tolerated. Both cross the blood-brain barrier. In our experimental models, the combination limited the appearance and number of brain metastases, which are often fatal.

III. Compositions of the Combination

Catechins

The herein describe combination therapy comprises the administration to the subject a catechin (e.g., a catechin ester), or a derivative or metabolite of the catechin. Catechins (flavan-3-ols) are antioxidants and natural phenols that are found in tea, some fruits, cocoa, and other plants. Catechins may also be synthesized chemically. Tea catechins are typically classified into two groups: epi-structured catechins (e.g., EGCG) and non-epi-structured catechins (e.g., GCG). Epi-structured catechins generally exist in higher amount in tea than the non-epi-structured catechins. Exemplary epi-structured catechins include, but are not limited to, epigallocatechin gallate (EGCG), epigallocatechin (EGC), epicatechin gallate (ECG), and epicatechin (EC). Exemplary non-epi-structured catechins include, without limitation, gallocatechin gallate (GCG), gallocatechin (GC), catechin gallate (CG), and catechin. In some embodiments, the combination therapy comprises an epi-structured catechin, e.g., EGCG. In some embodiments, the combination therapy comprises a non-epi-structured catechin, e.g., GCG. The level of various catechins in plants may be readily analyzed by suitable instrumentations such as gas chromatography (GC), mass spectrometry (MS), GC-MS, high-performance liquid chromatography (HPLC), and LC-MS/MS. In some embodiments, the combination therapy comprises a catechin in ester form; for example, EGCG is an ester of EGC with gallic acid. In some embodiments, the combination therapy comprises a catechin in phenol form, e.g., EGC. In some embodiments, the catechin used in the combination therapy is EGCG. In some embodiments, the catechin used in the combination therapy is ECG.

In some embodiments, the herein described catechins (e.g., catechin ester) or their derivatives or metabolites thereof contain one or more asymmetric centers and thus give rise to enantiomers, diastereomers, and other stereoisomeric forms that are defined, in terms of absolute stereochemistry, as (R)- or (S)-. It is intended that all stereoisomeric forms of the catechin or their derivatives or metabolites thereof are contemplated by this disclosure. Further, when the compounds described herein contain alkene double bonds, it is intended that this disclosure includes both E and Z geometric isomers (e.g., cis or trans). Likewise, all possible isomers, as well as their racemic and optically pure forms, and all tautomeric forms are also intended to be included. Some of the catechins possess two epimers (e.g., (±)-gallocatechin and (−)-gallocatechin), and accordingly both forms of the epimers are contemplated by the present disclosure. In some embodiments, the catechin used in the combination therapy is (−)-epigallocatechin gallate.

In some embodiments, the catechins (e.g., catechin ester) or their derivatives or metabolites thereof contain one or more tautomeric forms. A "tautomer" refers to a molecule wherein a proton shift from one atom of a molecule to another atom of the same molecule is possible. In circumstances where tautomerization is possible, a chemical equilibrium of the tautomers will exist, and the exact ratio of the tautomers depends on several factors, including physical state, temperature, solvent, and pH. It is intended that all tautomeric forms of the catechin or their derivatives or metabolites thereof are contemplated by this disclosure.

The catechins used herein can be naturally produced or chemically (or biochemically) synthesize. Methods of isolating catechins from plants are available in the art, e.g., as described in Vuong et al., Food Reviews International 27:227-247, 2011. Methods of synthesizing catechins are also known in the art, e.g., Liu et al., J. Org. Chem. 2008, 73(12), 4625-4629; Stadlbauer et al., Chem Commun (Camb), 2012 Aug. 28, 48(67) 8425-7.

In some embodiments, the combination therapy comprises a catechin derivative. A catechin derivative can refer to an ester of the catechin, e.g., an ethyl ester or fatty acid ester of EGCG. In some embodiments, the catechin derivative is an ester or polyester of EGCG/$C_2$-$C_9$ unsaturated or saturated fatty acid. In other embodiments, the catechin derivative is a mono-, di- or tri-glycerides of the catechin. In some embodiments, the catechin derivative is a pharmaceutically acceptable salt of the catechin. In further embodiments, the catechin derivative may be a sulfate, phosphate, acetate, formate, benzoate, or glycoside of the catechin.

In some embodiments, a catechin metabolite is used for the combination therapy. Exemplary catechin metabolites include 3'-O-methyl EGC; 4'-O-methyl EGC; 3'-O-methyl EC; 4'-O-methyl EC; 1-(3',4',5'-trihydroxyphenyl)-3-(2'',4'', 6''-trihydroxyphenyl)propan-2-ol; 1-(3',5'-dihydroxyphenyl)-3-(2'',4'',6''-trihydroxyphenyl)propan-2-ol; 3', 4', 5'-trihydroxyphenyl-γ-valerolactone; 5-(3',5'-dihydrophenyl)-γ-valerolactone; and 5-(3,5-dihydroxyphenyl)-4-hydroxyvaleric acid. Some representative catechin metabolites and methods of separating and analyzing catechins metabolites are known in the art, for example, as described in Schantz et al., Biotechnol. J. 2010(10): 1050-9; Takagaki et al., J. Agric Food Chem. 2010, 58(2):1313-21; and Green Tea Polyphenols (particularly, Chapter 3), Juneja et al., eds., version 20130315, CRC Press, which are hereby incorporated by reference in their entirety. A catechin derivative may also refer to a catechin oligomer, e.g., a dimer, trimer, or a tetramer of the catechin. In some embodiments, the catechin derivative used in the combination therapy is a dimer or trimer of EGCG.

In some embodiments, the catechin or a metabolite or derivative thereof is in a purified form. For instance, the catechin or a metabolite or derivative thereof may comprise at least 50%, 60%, 70%, 80%, 85%, 90%, 95%, 99%, or 99.9% EGCG by weight. In some embodiments, the catechin or a metabolite or derivative thereof comprises from about 85% to about 100%, from about 90% to about 100%, or from about 95% to about 99.99% EGCG by weight.

Nucleoside Analogue

The herein described combination therapy comprises the administration to the subject a nucleoside analogue. Nucleoside analogues are nucleosides that contain a nucleic acid analogue and a sugar. Nucleic acid analogues are compounds that are structurally similar to nucleic acids. Nucleoside analogues may be generally categorized into several types, including without limitation, deoxyuridine analogues, thymidine and deoxythymidine, guanosine and deoxyguanosine analogues, cytidine and deoxycytidine analogues, adenosine analogue, and deoxyadenosine analogues. Exemplary cytidine and deoxycytidine analogues include cytarabine, gemcitabine, emtricitabine, lamivudine, zalcitabine, azacitidine, and decitabine. Exemplary deoxyuridine analogues include idoxuridine and trifluridine. Exemplary thymidine or deoxythymidine analogues include stavudine, zidovudine, and telbivudine. In some embodiments, the nucleoside analogue used in the combination therapy is a DNA analogue. In other embodiments, the nucleoside analogue used in the combination therapy is an RNA analogue.

In some embodiments, the nucleoside analogue used in the combination therapy is cytarabine, gemcitabine, clofarabine, fludarabine, nelarabine, cladribine, 5-fluorouracil, azacytidine, decitabine, or capecitabine. In some embodiments, the nucleoside analogue used in the combination therapy is azacytidine or decitabine. In certain embodiments, two or more nucleoside analogues are used in the combination therapy. For example, in some embodiments, both azacytidine and decitabine are administered. In further embodiments, a derivative of the nucleoside analogue is used, e.g., glycosides of the nucleoside analogue.

IV. Method of Treatment

The methods and combination therapies described herein can be used to treat, prevent or inhibit progression of cancer cells in a subject in need thereof. The methods and compound combinations can also be used to stimulate a subject's immune system against cancer cells. The methods and compound combinations are useful in treating cancer or stimulating a subject's immune system, at least in part, due to their enhancement for or synergy with a cancer immunotherapy.

For example, the methods and combination therapies described herein can be used to inhibit progression of the cancer cells, to prevent progression of the cancer cells, to inhibit proliferation of the cancer cells, to decrease the number of the cancer cells, to promote apoptosis of the cancer cells, or to change the function of the cancer cells in a human subject in need thereof. Accordingly, the methods and combination therapies may be used for a subject that has been diagnosed as having cancer.

In some embodiments, the methods and compound combinations stimulate a subject's immune system against cancer. In certain embodiments, the immune stimulation is accomplished, at least in part, by reducing Wnt signaling, upregulating antigen presenting pathways (e.g., numerous genes; direct MHC staining), upregulating cancer antigens (e.g., NY-ESO1, MAGE A6, MageA3) presentation, inducing a viral mimicry response, upregulating the JAK-STAT pathway (P-STAT3), inducing an interferon signature gene (ISG) response which includes PDL-1 and MHC I and II expression, or any combination thereof. In some embodiments, the immune stimulation comprises reduction of Wnt signaling and proliferation. Wnt signaling pathways represent a group of signal transduction pathways that pass signals into a cell through cell surface receptors. Wnt signaling has been implicated in breast and other cancers. In some embodiments, either immune stimulation or inhibition of Wnt signaling comprises attenuation of a Warburg-like metabolism. Warburg effect refers to an increased aerobic glycolysis by cancer cells, which is a metabolic characteristic of cancer. Warburg effect is crucial for cancer cells to acquire energy for continued tumor proliferation. In some embodiments, the immune stimulation comprises augmenting JAK/STAT signaling. JAK/STAT signaling pathway communicates information from chemical signals outside of a cell to the cell nucleus, leading to an activation of genes through transcription. JAK/STAT signaling pathway plays an important role in enhancing antigen presentation and in regulation of PDL-1 and PDL-2 expression. In some embodiments, the immune stimulation comprises activating IFN signaling.

The methods and combination therapies may comprise an immunotherapy, such as monoclonal antibodies (e.g., checkpoint inhibitors), non-specific immunotherapy (e.g., interferons and interleukins), oncolytic virus therapy, T-cell therapy (e.g., CAR T-cell therapy), and cancer vaccine. In particular, the present disclosure is directed to methods and combination therapies of treating cancer comprising the steps of administering to a subject (1) a catechin ester or a derivative or metabolite thereof (e.g., EGCG), (2) a nucleoside analogue (e.g., DAC), and (3) a cancer immunotherapy. The cancer immunotherapy may be monoclonal antibodies, interferons, interleukins, oncolytic virus therapy, T-cell therapy (e.g., CAR T-cell therapy), cancer vaccine, or a combination of different immunotherapies. In some embodiments, the cancer immunotherapy comprises the administration of checkpoint inhibitors. In some embodiments, the cancer immunotherapy is a T-cell therapy, e.g., a CAR T-cell therapy.

Subjects

A suitable subject for the treatment may be a mammal such as human, dog, cat, horse, or any animal in which a cancer immunotherapy may potentially be desirable. In embodiments, the subject is a human.

In some embodiments, the cancer is a solid tumor. Exemplary solid tumors include, but are not limited to, breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas. Exemplary cancers may further include the ones have origins or metastases in breast, bone, lung, liver, brain, stomach, intestine, colorectal, prostate, ovarian, uterine, cervical, kidney, spine, smooth muscle, skeletal muscle, or any other human organ.

An exemplary list of cancers further include, but are not limited to, multiple myeloma, leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuro-blastoma, and retinoblastoma).

In embodiments, the subject has or is diagnosed with a breast cancer. The breast cancer may be non-invasive, invasive, and/or metastatic breast cancer. The breast cancer may also be one that is categorized as in situ, i.e., breast cancer that has not spread, or invasive or infiltrating, i.e., breast cancer that has spread into the surrounding breast tissue. Common in situ breast cancers include ductal carcinoma in situ and lobular carcinoma in situ. Common invasive breast cancers include invasive ductal carcinoma and invasive lobular carcinoma. The breast cancer may originate in the epithelial cells, in the glands, in the (milk) ducts, in the lobules (milk-producing glands), or in other tissue or cells. In embodiments, the breast cancer is adenocarcinoma, inflammatory breast cancer, sarcoma, phyllodes tumor, Paget disease, angiosarcoma, or a combination of different types.

In further embodiments, the cancer is a triple negative breast cancer. Triple negative breast cancer refers to a breast cancer, where the breast cancer cells are tested negative for estrogen receptors (ER−), progesterone receptors (PR−), and HER2 (HER2−). In embodiments, the breast cancer is one with metastases such as brain, bone, liver, or lung metastases.

In some embodiments, the subject is 5 to 75 years old. In some embodiments, the subject is 5 to 10, 5 to 15, 5 to 18, 5 to 25, 5 to 35, 5 to 45, 5 to 55, 5 to 65, 5 to 75, 10 to 15, 10 to 18, 10 to 25, 10 to 35, 10 to 45, 10 to 55, 10 to 65, 10 to 75, 15 to 18, 15 to 25, 15 to 35, 15 to 45, 15 to 55, 15 to 65, 15 to 75, 18 to 25, 18 to 35, 18 to 45, 18 to 55, 18 to 65, 18 to 75, 25 to 35, 25 to 45, 25 to 55, 25 to 65, 25 to 75, 35 to 45, 35 to 55, 35 to 65, 35 to 75, 45 to 55, 45 to 65, 45 to 75, 55 to 65, 55 to 75, or 65 to 75 years old. In some embodiments, the subject is at least 5, 10, 15, 18, 25, 35, 45, 55, or 65 years old. In some embodiments, the subject is at most 10, 15, 18, 25, 35, 45, 55, 65, or 75 years old.

Checkpoint Inhibitors

Immune checkpoints are inhibitory pathways that slow down or stop immune reactions and prevent excessive tissue damage from uncontrolled activity of immune cells. A checkpoint inhibitor may refer to any small molecule chemical compound, antibody, nucleic acid molecule, or polypeptide, or fragments thereof, which blocks the inhibitory pathways, allowing more extensive immune activity. Three important types of checkpoint inhibitors target the molecules cytotoxic T-lymphocyte-associated protein 4 (CTLA-4), programmed cell death protein 1 (PD-1), and programmed death-ligand 1 (PD-L1). In some embodiments, the checkpoint inhibitor is targeted at another member of the CD28/CTLA4 Ig superfamily such as BTLA, LAG3, ICOS, PDL1 or MR. Page et al., Annual Review of Medicine 65:27 (2014). In some cases targeting a checkpoint inhibitor is accomplished with an inhibitory antibody or similar molecule. In other cases, it is accomplished with an agonist for the target.

In some embodiments, the checkpoint inhibitor is an inhibitor of CTLA-4, such as an anti-CTLA-4 antibody. In some embodiments, the anti-CTLA4 antibody is Ipilimumab (Yervroy®, Bristol-Myers Squibb Company, NY), a monoclonal antibody that targets CTLA-4. Anti-CTLA-4 antibody, or ipilimumab, can be a recombinant, human monoclonal antibody that binds to the CTLA-4 and blocks the interaction of CTLA-4 with its ligands, CD80/CD86.

In some embodiments, the checkpoint inhibitor is an inhibitor of PD-1, such as an anti-PD-1 antibody. In some embodiments, the anti-PD-1 antibody is nivolumab.

Nivolumab (Opdivo®, Bristol-Myers Squibb Company, NY) is a human immunoglobulin G4 (IgG4) mAb that binds to the programmed death 1 (PD-1) receptor and blocks its interaction with PD-L1 and programmed death ligand 2 (PD-L2), reversing PD-1 pathway-mediated inhibition of the immune response, including the anti-tumor immune response. In some embodiments, the anti-PD-1 antibody is pembrolizumab (Keytruda®). Pembrolizumab is a humanized IgG4 antibody that targets the PD-1 receptor of lymphocytes.

In some embodiments, the checkpoint inhibitor is an inhibitor of PD-L1, such as an anti-PD-L1 antibody. In some embodiments, the anti-PD-L1 antibody is Atezolizumab (Tecentriq®), Avelumab (Bavencio®), Durvalumab (Imfinzi®), or Keytruda (Pembrolizumab®).

In addition to CTLA-4 and PD-1/PD-L1 molecules, various other immunomodulatory targets have been identified preliminarily, many with corresponding therapeutic antibodies that are being investigated in clinical trials. Page et al. (Annu. Rev. Med. 2014.65) details targets of antibody immune modulators in FIG. 1, which is hereby incorporated by reference, Accordingly, the present invention features in exemplary embodiments, combinations of (1) a catechin ester or a derivative or metabolite thereof (e.g., EGCG), (2) a nucleoside analogue (e.g., DAC), and (3) a checkpoint inhibitor such as Ipilimumab, pembrolizumab, or Nivolumab.

In further embodiments, the inhibitor is targeted at a member of the tumor necrosis factor receptor (TNFR) superfamily such as CD40, OX40, CD137, GITR, CD27 or TIM-3. In some cases the inhibitor is an antibody or similar molecule. In other cases, the inhibitor is an agonist for the target, for example, a CD40 agonist such as AP005M and selicrelumab (RG7876). In embodiments, the combination therapy may comprise more than one checkpoint inhibitor. For example, the immunotherapy may comprise an anti-PD-1 antibody and a CD40 agonist, an anti-PD-L1 antibody and a CD40 agonist, or a CTLA-4 inhibitor and a PD-1 inhibitor.

T-Cell Therapy

T-cell therapies, particularly those use T-cells with a chimeric antigen receptor (CAR), redirect the genetically engineered T-cells to a suitable surface molecule on cancer cells. These T-cell therapies have shown promising results in harnessing the power of the immune system to treat B cell malignancies (see, e.g., Sadelain et al., Cancer Discovery 3:388-398 (2013)). The clinical results with CD-19-specific CAR T-cells (called CTL019) have shown complete remissions in patients suffering from chronic lymphocytic leukemia (CLL) as well as in childhood acute lymphoblastic leukemia (ALL) (see, e.g., Kalos et al., Sci Transl Med 3:95ra73 (2011), Porter et al., NEJM 365:725-733 (2011), Grupp et al., NEJM 368:1509-1518 (2013)). An alternative approach is the use of T-cell receptor (TCR) alpha and beta chains selected for a tumor-associated peptide antigen for genetically engineering autologous T-cells. These TCR chains will form complete TCR complexes and provide the T-cells with a TCR for a second defined specificity. Encouraging results were obtained with engineered autologous T-cells expressing NY-ESO-1-specific TCR alpha and beta chains in patients with synovial carcinoma.

T-cells may be activated and expanded generally using methods as described, for example, in U.S. Pat. Nos. 6,352, 694; 6,534,055; 6,905,680; 6,692,964; 5,858,358; 6,887, 466; 6,905,681; 7,144,575; 7,067,318; 7,172,869; 7,232, 566; 7,175,843; 5,883,223; 6,905,874; 6,797,514; 6,867, 041, and 7,572,631. Generally, the T-cells used in the combination therapy may be expanded by contact with a surface having attached thereto an agent that stimulates a CD3/TCR complex associated signal and a ligand that stimulates a costimulatory molecule on the surface of the T-cells. In particular, T-cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T-cells, a ligand that binds the accessory molecule is used. For example, a population of T-cells can be contacted with an anti-CD3 antibody and an anti-CD28 antibody, under conditions appropriate for stimulating proliferation of the T-cells. To stimulate proliferation of either CD4+ T-cells or CD8+ T-cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9): 13191328, 1999; Garland et al., J. Immunol. Meth. 227(1-2):53-63, 1999).

T-cells that have been exposed to varied stimulation times may exhibit different characteristics. For example, typical blood or apheresed peripheral blood mononuclear cell products have a helper T-cell population (TH, CD4+) that is greater than the cytotoxic or suppressor T-cell population (TC, CD8+). Ex vivo expansion of T-cells by stimulating CD3 and CD28 receptors produces a population of T-cells that prior to about days 8-9 consists predominately of TH cells, while after about days 8-9, the population of T-cells comprises an increasingly greater population of TC cells.

The herein described compound combination may be used in combination with a T-cell therapy, e.g., CAR T-cell therapy. For instance, in some embodiments, the FDA-approved CAR T-cell therapies may be used in the combination therapy, which include, without limitation, tisagenlecleucel (KYMRIAH™) and axicabtagene ciloleucel (YESCARTA™). Tisagenlecleucel is suitable for treatment of relapsed or refractory acute lymphoblastic leukemia and for relapsed or refractory diffuse large B-cell lymphoma. Axicabtagene ciloleucel is suitable for treatment of several types of relapsed or refractory large B-cell lymphoma non-Hodgkin lymphomas.

In some embodiments, the CAR T-cell therapy used in the combination is directed to a cancer-associated antigen. In some embodiments, the CAR T-cell therapy used in the combination is directed to CD8, CD4, CD19, CD22, CD123, NY-ESO1, Mage-A3, MAGE A6, mucin1, cMET, TEM8, MART-1, gp100, CEA, hTERT, EGFR, mesothelin, HPV, EBV, MCC, B-catenin, CDK4, ERBB2IP, or a combination thereof. In some embodiments, the CAR T-cell therapy is directed to mucin1 (MUC1) (see Bajgain, J. Immunotherapy of Cancer 2018 6:34. In other embodiments, the CAR T-cell therapy is directed to cMET, such as the ones used in clinical trial NCT03060356, CAR-T Cell Immunotherapy for Triple Negative Breast Cancer. In some embodiments, the CAR T-cell therapy is directed to CD19. In some embodiments, the CAR T-cell therapy is directed to NY-ESO1, e.g., described in Patel et al. Blood 2014, 124:3843.

Accordingly, in embodiments, the combination therapy comprises administering an effective amount of a cell expressing at least one CAR. In some embodiments, the cell expresses at least one CAR directed to a cancer-associated antigen. In some instances, the cell is an autologous T-cell. In some instances, the cell is an allogeneic T-cell. In some embodiments, the combination therapy comprises administering CAR-T cells directed to CD19, Mage-A3, MAGE A6, NY-ESO1, or a combination thereof.

Administration Schedule

The present invention is directed to methods of treating cancer or stimulating immune system by administering an effective amount of the compound combination of (1) a catechin ester or a derivative or metabolite thereof (e.g., EGCG) and (2) a nucleoside analogue (e.g., DAC) according to the present invention (including a pharmaceutically acceptable salt, thereof). The present compound combination may be administered in combination with a cancer immunotherapy.

The compositions may be administered once daily, twice daily, once every two days, once every three days, once every four days, once every five days, once every six days, once every seven days, once every two weeks, once every three weeks, once every four weeks, once every two months, once every six months, or once per year. The dosing interval can be adjusted according to the needs of individual patients. For longer intervals of administration, extended release or depot formulations can be used.

In certain embodiments, the compounds of the invention are administered for time periods exceeding two weeks, three weeks, one month, two months, three months, four months, five months, six months, one year, two years, three years, four years, or five years, ten years, or fifteen years; or for example, any time period range in days, months or years in which the low end of the range is any time period between 14 days and 15 years and the upper end of the range is between 15 days and 20 years (e.g., 4 weeks and 15 years, 6 months and 20 years). In some cases, it may be advantageous for the compounds of the invention to be administered for the remainder of the patient's life. In some embodiments, the patient is monitored to check the progression of the disease or disorder, and the dose is adjusted accordingly.

As used herein, the term "fixed intermittent dosing regimen" refers to repeating cycles of preplanned drug administration in which the drug is administered on one or more consecutive days ("days on") followed by one or more consecutive days of rest on which the drug is not administered ("days off"). In some embodiments, the cycles are regular, in that the pattern of days on and days off is the same in each cycle. In some embodiments, the cycles are irregular, in that the pattern of days on and days off differs from one cycle to the next cycle. In some embodiments, each of the repeating cycles, however, is preplanned in that it is not determined solely in response to the appearance of one or more adverse events. In some embodiments, administration of the composition comprising the catechin ester or a derivative or metabolite thereof and/or the nucleoside analogue is repeated for one to ten cycles, such as for example one cycle, two cycles, three cycles, four cycles, five cycles, six cycles, seven cycles, eight cycles, nine cycles or ten cycles. In some embodiments, a cycle comprises 3 days to 60 days. In some embodiments, a cycle comprises 7 to 50 days, such as 7 to 30 days, 7 to 21 days, or 7 to 14 days. In some embodiments, a cycle consists of 7 days.

In some embodiments, the fixed intermittent dosing regimen comprises a repeating cycle of administration of an effective amount of said combination therapy, or one or more components of the combination therapy on 1 to 10 consecutive days, such as 2 to 5 consecutive days, followed by 6 to 2 days of rest, such as 5 to 2 days of rest. In some embodiments, the administration of the combination therapy comprises one or more fixed intermittent dosing regimen.

In embodiments, the catechin ester or a derivative or metabolite thereof and the nucleoside analogue are administered on the same day, the same week, or the same month. In certain embodiments, the catechin ester or a derivative or metabolite thereof, the nucleoside analogue, and the immunotherapy are administered on the same day, the same week, or the same month. In some embodiments, the catechin ester or a derivative or metabolite thereof and the nucleoside analogue are administered within 1 hour, 2 hours, 3 hours, 4 hours, 5 hours, 6 hours, 12 hours, or 1 day. In some embodiments, the catechin ester or a derivative or metabolite thereof and the nucleoside analogue are administered simultaneously. In further embodiments, the catechin ester or a derivative or metabolite thereof, the nucleoside analogue, and the immunotherapy are administered simultaneously. Simultaneous administrations may be performed by the same or different routes of administration.

In embodiments, the catechin ester or a derivative or metabolite thereof, the nucleoside analogue, and the immunotherapy are administered sequentially. In some embodiments, the catechin ester or a derivative or metabolite thereof and the nucleoside analogue are administered alternately; for example, only one component is administered for a consecutive period of time. In some embodiments, the catechin ester or a derivative or metabolite thereof and the nucleoside analogue are administered on alternating weeks or alternating days.

In some embodiments, the administration of the catechin ester or a derivative or metabolite thereof, the nucleoside analogue, or both are initiated before the initiation of the immunotherapy. In some embodiments, the administration of the catechin ester or a derivative or metabolite thereof, the nucleoside analogue, or both are initiated after the initiation of the immunotherapy. In other embodiments, the administration of the catechin ester or a derivative or metabolite thereof, the nucleoside analogue, and the immunotherapy are initiated on the same day, in the same week, or in the same month.

In certain embodiments, the catechin ester or a derivative or metabolite thereof, the nucleoside analogue, or both are administered indefinitely after initiation. In other embodiments, the catechin ester or a derivative or metabolite thereof, the nucleoside analogue, or both are administered over a period of at least 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 20 weeks, 30 weeks, 40 weeks, 50 weeks, 1 year, or 2 years. In some embodiments, the catechin ester or a derivative or metabolite thereof, the nucleoside analogue, or both are administered over a period of at most 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 20 weeks, 30 weeks, 40 weeks, 50 weeks, 1 year, or 2 years.

In embodiments, the catechin ester or a derivative or metabolite thereof, the nucleoside analogue, or both are administered 1, 2, 3, 4, 5 or more times a day or 1, 2, 3, 4, 5, 6, 7 or more times a week. In some embodiments, the catechin ester or a derivative or metabolite thereof, the nucleoside analogue, or both are administered every 6 hours, 12 hours, or 24 hours.

In certain embodiments, the catechin ester or a derivative or metabolite thereof, the nucleoside analogue, or both are administered on consecutive days. For example, the nucleoside analogue and/or the catechin ester or a derivative or metabolite thereof may be administered for 1, 2, 3, 4, 5, 6, 7, 8, 9, 10, 11, 12, 13, 14, 15, 16, 17, 18, 19, 20, 21, 22, 23, 24, 25, or more consecutive days. In embodiments, the dose of compound administered on different days of the consecutive days of treatment may be the same or different. In some specific embodiments, the compounds are administered on 5, 7, or 10 consecutive days.

In certain specific embodiments, the catechin ester or a derivative or metabolite thereof, the nucleoside analogue, or both are initiated at least about 1 hour, 2 hours, 4 hours, 6 hours, 12 hours, 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, or 10 weeks before the initiation of the immunotherapy. In some embodiments, the catechin ester or a derivative or metabolite thereof, the nucleoside analogue, or both are initiated at most 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, or 10 weeks after the initiation of the immunotherapy.

Pharmaceutical Composition and Method of Delivery

Disclosed herein are pharmaceutical compositions comprising the compound combination of (a) a catechin ester or a derivative or metabolite thereof and (2) a nucleoside analogue. The pharmaceutical composition may further comprise an immunotherapy, such as a checkpoint inhibitor or CAR T-cell therapy.

Pharmaceutical compositions comprise the herein-described combination therapy in a therapeutically effective amount for treating diseases and conditions (e.g., a breast cancer), which have been described herein, optionally in combination with a pharmaceutically acceptable additive, carrier and/or excipient. One of ordinary skill in the art from this disclosure and the knowledge in the art will recognize that a therapeutically effective amount of one of more compounds according to the present invention may vary with the condition to be treated, its severity, the treatment regimen to be employed, the pharmacokinetics of the agent used, as well as the patient (animal or human) treated.

Compositions are formulated, dosed, and administered in a fashion consistent with good medical practice. The compounds of the current disclosure may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. The term parenteral as used herein includes subcutaneous, intravenous, intramuscular, intrasternal, intraperitoneal, and infusion techniques. The term parenteral also includes injections, into the eye or ocular, intravitreal, intrabuccal, transdermal, intranasal, into the brain, including intracranial and intradural, into the joints, including ankles, knees, hips, shoulders, elbows, wrists, directly into tumors, and the like, and in suppository form.

The compounds of the present disclosure may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical composition is prepared by mixing a compound of the present disclosure and a carrier or excipient. Suitable carriers and excipients are well known to those skilled in the art and are described in detail in, e.g., Ansel, Howard C, et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The compositions may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present disclosure or pharmaceutical composition thereof) or aiding the manufacturing of the pharmaceutical product (i.e., medicament).

In embodiments, at least one component of the pharmaceutical composition is provided in a solid form, such as a lyophilized powder suitable for reconstitution, a liquid solution, suspension, emulsion, tablet, pill, capsule, sustained release formulation, or powder.

In embodiments, for solid dosage forms used in oral administration (e.g., capsules, tablets, pills, dragees, powders, granules and the like), the active ingredient is mixed with one or more pharmaceutically acceptable carriers, excipients, or diluents, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents, in the case of capsules, tablets, and pills, the pharmaceutical compositions can also comprise buffering agents. Solid compositions of a similar type can also be prepared using fillers in soft and hard-filled gelatin capsules, and excipients such as lactose or milk sugars, as well as high molecular weight polyethylene glycols and the like.

In one embodiment, the active compounds are prepared with carriers that protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid, and polylactic-co-glycolic acid (PLGA). Methods of formulating such slow or controlled release compositions of pharmaceutically active ingredients, are known in the art and described in several issued US Patents, some of which include, but are not limited to, U.S. Pat. Nos. 3,870,790; 4,226,859; 4,369,172: 4,842,866 and 5,705,190, the disclosures of which are incorporated herein by reference in their entireties. Coatings can be used for delivery of compounds to the intestine (see, e.g., U.S. Pat. Nos. 6,638,534, 5,541, 171, 5,217,720, and 6,569,457, and references cited therein).

The active compound or pharmaceutically acceptable salt thereof may also be administered as a component of an elixir, suspension, syrup, wafer, chewing gum or the like. A syrup may contain, in addition to the active compounds, sucrose or fructose as a sweetening agent and certain preservatives, dyes and colorings and flavors, In embodiments, at least one component of the pharmaceutical composition is supplied in liquid form, for example, in a sealed container indicating the quantity and concentration of the active ingredient in the pharmaceutical composition. In related embodiments, the liquid form of the pharmaceutical composition is supplied in a hermetically sealed container.

For parenteral formulations, the carrier usually comprises sterile water or aqueous sodium chloride solution, though other ingredients including those which aid dispersion may be included. Of course, where sterile water is to be used and maintained as sterile, the compositions and carriers are also sterilized. Injectable suspensions may also be prepared, in which case appropriate liquid carriers, suspending agents and the like may be employed. The parenteral preparation can be enclosed in ampoules, disposable syringes or multiple dose vials made of glass or plastic. If administered intravenously, carriers can include, for example, physiological saline or phosphate buffered saline (PBS).

Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

In some embodiments, at least one component of the combination therapy is administered orally, topically, parenterally, or by inhalation. In some embodiments, all of the components of the combination therapy are administered orally, topically, parenterally, or by inhalation. In other embodiments, not all of the components of the combination therapy are administered by the same route, e.g., one component is administered orally and another is administered parenterally. In further embodiments, the catechin ester or a derivative or metabolite thereof, the nucleoside analogue, or both are administered orally or by injection.

In certain embodiments, the cancer immunotherapies such as checkpoint inhibitors and T-cell therapies are administered parenterally, orally, or by inhalation. For example, checkpoint inhibitors and T-cell therapies may be administered by intravenous or subcutaneous injection. In certain embodiments, the catechin ester or a derivative or metabolite thereof is administered orally or by injection. In some embodiments, the EGCG is administered orally, e.g., as a tablet or a capsule. In some embodiments, the EGCG is administered by intravenous injection, subcutaneous injection, or by infusion. In certain embodiments, the nucleoside analogue is administered intravenously or orally. For example, in some embodiments, the nucleoside analogue (e.g., DAC) is administered orally. For another example, in some embodiments, the nucleoside analogue (e.g., DAC) is administered by IV-infusion.

Dosage

When the agents or components of the combination therapy described herein are administered as pharmaceuticals to humans or animals, they can be given per se or as a pharmaceutical composition containing active ingredient in combination with a pharmaceutically acceptable carrier, excipient, or diluent.

Actual dosage levels and time course of administration of the active ingredients in the pharmaceutical compositions of the invention can be varied so as to obtain an amount of the active ingredient which is effective to achieve the desired therapeutic response for a particular patient, composition, and mode of administration, without being toxic to the patient.

Determination of an effective amount is well within the capability of those skilled in the art, especially in light of the detailed disclosure provided herein. Generally, an efficacious or effective amount of an agent is determined by first administering a low dose of the agent(s) and then incrementally increasing the administered dose or dosages until a desired effect (e.g., reduce or eliminate symptoms associated with viral infection or autoimmune disease) is observed in the treated subject, with minimal or acceptable toxic side effects. Applicable methods for determining an appropriate dose and dosing schedule for administration of a pharmaceutical composition of the present invention are described, for example, in Goodman and Oilman's The Pharmacological Basis of Therapeutics, Goodman et al., eds., 11th Edition, McGraw-Hill 2005, and Remington: The Science and Practice of Pharmacy, 20th and 21st Editions, Gennaro and University of the Sciences in Philadelphia, Eds., Lippencott Williams & Wilkins (2003 and 2005), each of which is hereby incorporated by reference.

A dose of an agent can be the maximum that a patient can tolerate and not develop serious or unacceptable side effects. The maximum tolerance dose may be determined by an up-titration, or does escalation study. During up-titration, a subject is initially administered a low does for a period of time, and the care provider will assess the subject's response to the drug, the subject's tolerance to the drug, and the adverse effect of the drug on the patients. Assuming the subject can tolerant the initial dose, the care provider may then gradually increase the dose upward to an adequate level, or until the maximum dose that the subject can tolerant has been reached.

In embodiments, the doses of one or more components of the combination therapy are determined by up-titration. For example, the dose of the catechin ester or a derivative or metabolite thereof may be determined by up-titration. For another example, the dose of the EGCG is determined by up-titration with an initial dose of about 50 mg, 100 mg, 200 mg, 300 mg, 400 mg, 500 mg, 600 mg, 700 mg, 800 mg, 900 mg, 1000 mg or more. For yet another example, the up-titration of the catechin ester or a derivative or metabolite thereof comprises dose levels of about 800 mg, 1200 mg, and 1600 mg.

Unit dosage formulations can be those containing a daily dose or unit, daily sub-dose, as herein discussed, or an appropriate fraction thereof, of the administered ingredient.

The dosage regimen for treating a disorder or a disease with the compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods.

The amounts and dosage regimens administered to a subject can depend on a number of factors, such as the mode of administration, the nature of the condition being treated, the body weight of the subject being treated and the judgment of the prescribing physician; all such factors being within the ambit of the skilled artisan from this disclosure and the knowledge in the art. The amount of compound included within therapeutically active formulations according to the present invention is an effective amount for treating the disease or condition.

In general, a therapeutically effective amount of a compound in dosage form can range from slightly less than about 0.025 mg/kg/day to about 2.5 g/kg/day, about 0.1 mg/kg/day to about 100 mg/kg/day of the patient or considerably more, depending upon the compound used, the condition or infection treated and the route of administration, although exceptions to this dosage range may be contemplated by the present invention.

According to certain exemplary embodiments, the catechin ester or a derivative or metabolite thereof is administered at least about 0.05 mg/kg, 0.1 mg/kg, 0.5 mg/kg, 1 mg/kg, 2 mg/kg, 3 mg/kg, 4 mg/kg, 5 mg/kg, 6 mg/kg, 7 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 50 mg/kg, 100 mg/kg, or 200 mg/kg per administration. In some embodiments, the catechin ester or a derivative or metabolite thereof is administered at least about 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg.

According to certain exemplary embodiments, the catechin ester or a derivative or metabolite thereof is administered at most about 5 mg/kg, 6 mg/kg, 7 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 50 mg/kg, 100 mg/kg, 100 mg/kg, or 1000 mg/kg per administration. In some embodiments, the catechin ester or a derivative or metabolite thereof is administered at most about 10 mg/kg, 15 mg/kg, 20 mg/kg, 25 mg/kg, 30 mg/kg, 50 mg/kg, 100 mg/kg, 100 mg/kg, or 1000 mg/kg.

According to certain exemplary embodiments, the catechin ester or a derivative or metabolite thereof is administered at least about 50 mg, 100 mg, 200 mg, 300 mg, 400 mg, 500 mg, 600 mg, 700 mg, 800 mg, 900 mg, 1000 mg, 1100 mg, 1200 mg, 1300 mg, 1400 mg, or 1500 mg. In some embodiments, the catechin ester or a derivative or metabolite thereof is administered at most about 200 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, or 5000 mg. In some specific embodiments, the catechin ester or a derivative or metabolite thereof is administered at a dosage that is from about 600 mg to about 1600 mg, from about 800 mg to about 1400 mg, or from about 1000 mg to about 1200 mg.

According to certain exemplary embodiments, the nucleoside analogue is administered at least about 0.05 mg/m², 0.15 mg/m², 0.5 mg/m², 1 mg/m², 1.5 mg/m², 2 mg/m², 5 mg/m², 10 mg/m², 11 mg/m², 12 mg/m², 13 mg/m², 14 mg/m², 15 mg/m², 16 mg/m², 17 mg/m², 18 mg/m², 19 mg/m², 20 mg/m², 30 mg/m², 40 mg/m², 50 mg/m², or 100 mg/m² per administration. In some embodiments, the nucleoside analogue is administered at least about 10 mg/m², 15 mg/m², 16 mg/m², 17 mg/m², 18 mg/m², 19 mg/m², 20 mg/m², or 50 mg/m².

According to certain exemplary embodiments, the nucleoside analogue is administered at most about 2 mg/m², 10 mg/m², 11 mg/m², 12 mg/m², 13 mg/m², 14 mg/m², 15 mg/m², 16 mg/m², 17 mg/m², 18 mg/m², 19 mg/m², 20 mg/m², 30 mg/m², 40 mg/m², 50 mg/m², 100 mg/m², 200 mg/m², or 500 mg/m² per administration. In some embodiments, the nucleoside analogue is administered at most about 10 mg/m², 15 mg/m², 20 mg/m², 30 mg/m², 40 mg/m², 50 mg/m², 100 mg/m², or 200 mg/m². In certain embodiments, the nucleoside analogue is administered at about 10-30 mg/m$^2$, 15-25 mg/m$^2$, or 16-20 mg/m$^2$.

According to certain exemplary embodiments, the nucleoside analogue is administered at least about 0.5 mg, 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, 45 mg, 50 mg, 60 mg, 70 mg, 80 mg, 90 mg, 100 mg, or 200 mg per administration. According to certain exemplary embodiments, the nucleoside analogue is administered at most about 5 mg, 10 mg, 15 mg, 20 mg, 25 mg, 30 mg, 35 mg, 40 mg, 50 mg, 60 mg, 70 mg, 80 mg, 90 mg, 100 mg, 200 mg, or 300 mg per administration. In certain embodiments, the nucleoside analogue is administered at about 10-50 mg, 15-40 mg, or 25-35 mg.

Accordingly, in some embodiments, the weight ratio of the catechin ester or a derivative or metabolite thereof to the nucleoside analogue is at least about 0.5:1, 1:1, 2:1, 4:1, 5:1, 10:1, 20:1, 30:1, 40:1, 50:1, 60:1, 70:1, 80:1, 90:1, 100:1, 200:1, 400:1, 500:1, or 1000:1. In some embodiments, the weight ratio of the catechin ester or a derivative or metabolite thereof to the nucleoside analogue is at most about 2:1, 4:1, 5:1, 10:1, 20:1, 30:1, 40:1, 50:1, 60:1, 70:1, 80:1, 90:1, 100:1, 200:1, 400:1, 1000:1, or 4000:1. In some embodiments, the weight ratio of the catechin ester or a derivative or metabolite thereof to the nucleoside analogue is from about 1:1 to about 100:1, from about 10:1 to about 90:1, from about 10:1 to about 80:1, from about 10:1 to about 70:1, from about 10:1 to about 60:1, from about 10:1 to about 50:1, from about 20:1 to about 40:1, or from about 25:1 to about 35:1.

In certain exemplary embodiments, the inhibitor, such as a checkpoint inhibitor or CD40 agonist, is administered at a dose of about 0.1-10 mg/kg. According to certain exemplary embodiments, the anti-CTLA4 antibody ipilimumab is administered at a dose of about 1 mg kg-3 mg/kg. For example, in certain exemplary embodiments, Nivolumab is given dosing at the standard single agent dosing level of 3 mg/kg. According to certain exemplary embodiments, the anti-CD40 antibody APX500M is administered at a dose of about 0.05 mg kg-10 mg/kg, for example, 0.1 mg/kg-2 mg/kg. Inhibitors, such as a checkpoint inhibitor or CD40 agonist, may be diluted before administration to a subject.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Kits

In an aspect, the invention provides kits containing any one or more of the elements discussed herein to allow administration of the combination therapy. Elements may be provided individually or in combinations, and may be provided in any suitable container, such as a vial, a bottle, or a tube. In some embodiments, the kit includes instructions in one or more languages, for example in more than one language. In some embodiments, a kit comprises one or more reagents for use in a process utilizing one or more of the elements described herein. Reagents may be provided in any suitable container. For example, a kit may provide one or more delivery or storage buffers. Reagents may be provided in a form that is usable in a particular process, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline.

The kit may advantageously allow the provision of all elements of the combination therapy of the invention. The kit may include any of the components above (e.g., a catechin ester or a derivative or metabolite thereof, a nucleoside analogue, and an immunotherapy) as well as instructions for use with any of the methods of the present invention.

In one embodiment the kit contains at least one vial with a component of the immunotherapy in liquid or lyophilized form. In one embodiment the kit may comprise ready to use components that are mixed and ready to administer. In one aspect a kit contains the catechin ester or a derivative or metabolite thereof in tablet or capsule form. In one aspect a kit contains the nucleoside analogue in solid form for oral administration or in liquid form for injection.

Although the present invention and its advantages have been described in detail, it should be understood that various changes, substitutions and alterations can be made herein without departing from the spirit and scope of the invention as defined in the appended claims.

The present invention is further illustrated in the following Examples which are given for illustration purposes only and are not intended to limit the invention in any way.

EXAMPLES

Example 1—Effect of EGCG/DAC on Tumor Growth

Figure 1B:
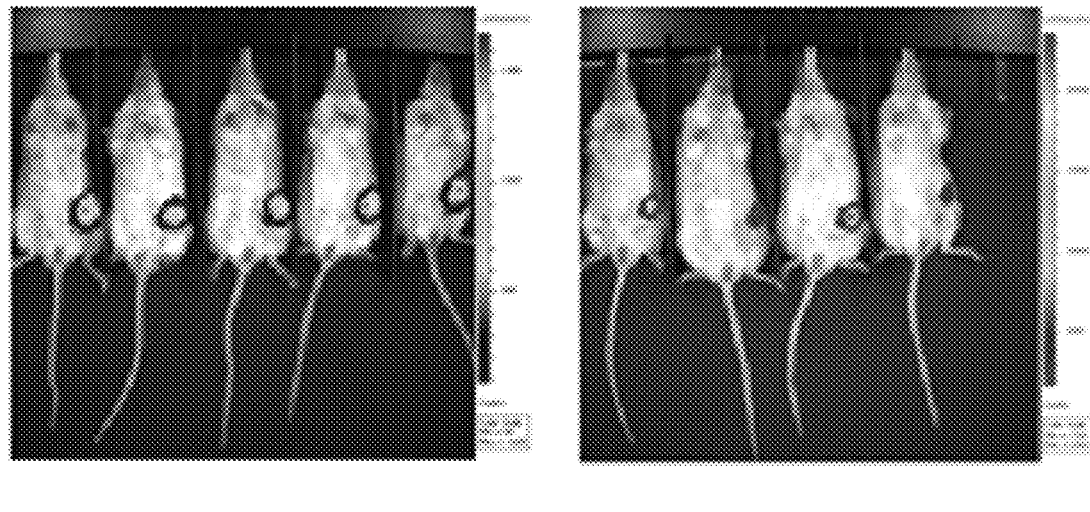

EGCG and DAC act synergistically on suppressing tumor growth. As shown in FIG. 1A, the LM1 subclone of MDA-MB-231 cells tagged with luciferase was implanted orthotopically into NOD-SCID mice. At least 5 mice were treated daily on alternative days with EGCG (16.5 mg/kg) and DAC (0.5 mg/kg) for the indicated time. Tumors were measured with calipers. FIG. 1B shows the bioluminescence imaging of EGCG and DAC treated xenograft mice. Treatment reduced the primary tumor size prone to metastasis compared to the untreated group. After allowing implanted IS13-cell (A GFP- and luciferase-labelled derivative of MDA-MB-231 cells) tumors to grow for approximately 3 weeks, mice were anesthetized with isofluorane and injected intra-peritoneally with 90 µl of luciferin.

Example 2—Effect of EGCG/DAC on Tumor Metastases

Figure 2:
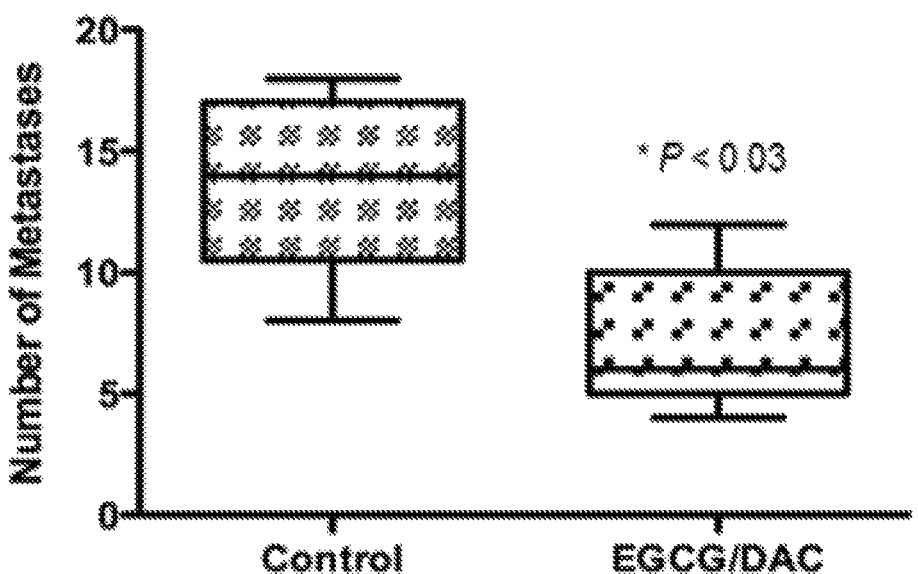
FIG. 2 illustrates the effect of EGCG/DAC on brain metastases in a TNBC human xenograft (immune compromised) mouse model.

As shown in FIG. 2, IS13 (MDA-MB-231 derivative cells, see Example 1) was implanted orthotopically into NOD-SCID mice. At least 6 mice were treated with EGCG (16.5 mg/kg) and DAC (0.5 mg/kg) and 5 mice treated with saline for the indicated time. Orthotopic implants of the IS13 brain-metastasizing variant of MDA-MB-231 cells, tagged with GFP, were treated with EGCG/DAC or saline for 2 weeks, followed by surgical resection of the tumor. GFPlabeled metastatic foci were counted on dissected brains 6 weeks following treatment and tumor resection.

Figure 3A:
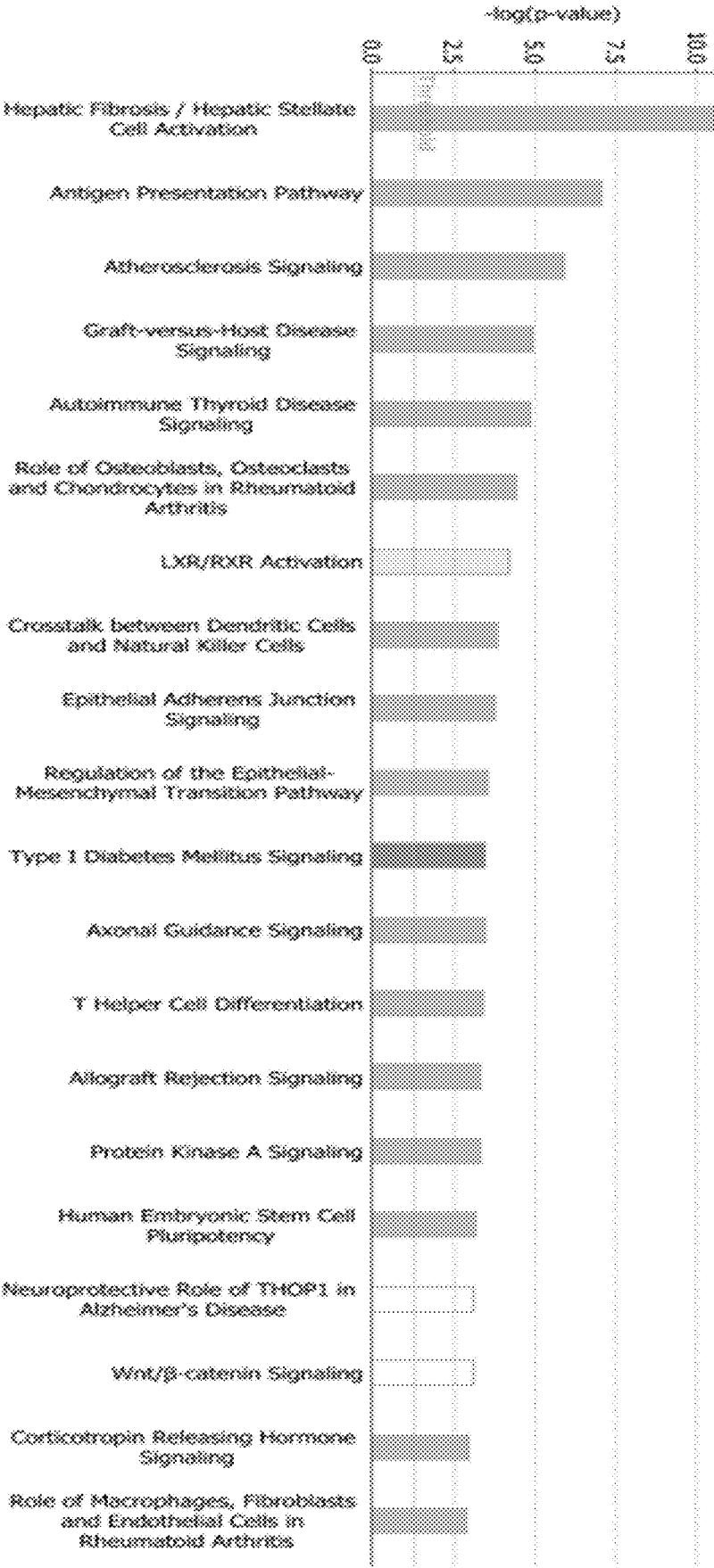
FIG. 3A and FIG. 3B illustrate an Ingenuity Pathway Analysis (IPA) of control and treated TNBC xenograft (immune compromised) tumors.
Figure 3B:

Example 3—Ingenuity Pathway Analysis (IPA) of Control and Treated TNBC Xenograft (Immune Compromised) Tumors RNA from the tumors in FIG. 1A and FIG. 1B were subjected to RNA Seq. The data was analyzed by IPA. The unbiased IPA results are depicted in FIG. 3A and FIG. 3B. As shown in FIG. 3A, the top 20 signaling pathways by p-value affected by EGCG/DAC are displayed. FIG. 3B shows the same top 20 signaling pathways with the fractional activation or inhibition by EGCG/DAC. Dark grey in the bars and black arrows indicate activated immune function, indicating upregulation of the genes involved in anti-tumor immune response. Light grey and white arrows indicate the Wnt signaling pathway is downregulated, confirming the proposed mechanism of the compound combination (see Example 25).

Example 4—Effect of EGCG/DAC on Wnt Signaling

Figure 4A:
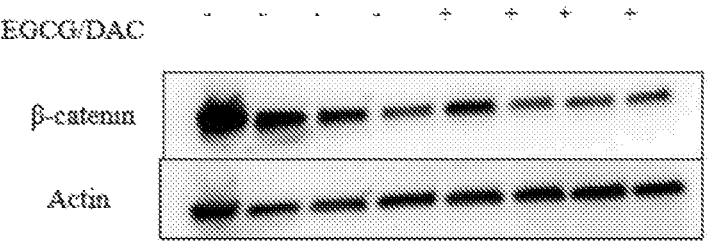
FIG. 4A illustrates a western blot of β-catenin and internal control actin from tumors dissected from control (−) and EGCG/DAC treated (+) MDA-MB-231 human xenografts.
Figure 4B:
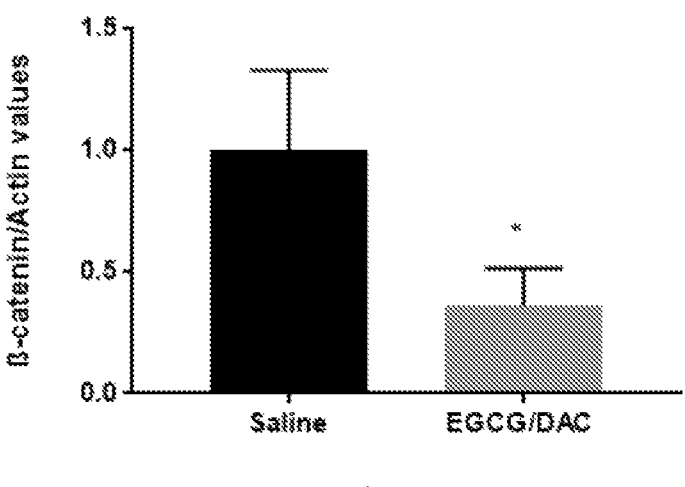
FIG. 4B illustrates a quantification graph combining data from three western blot each with 4 untreated and four treated samples.
Figure 4C:
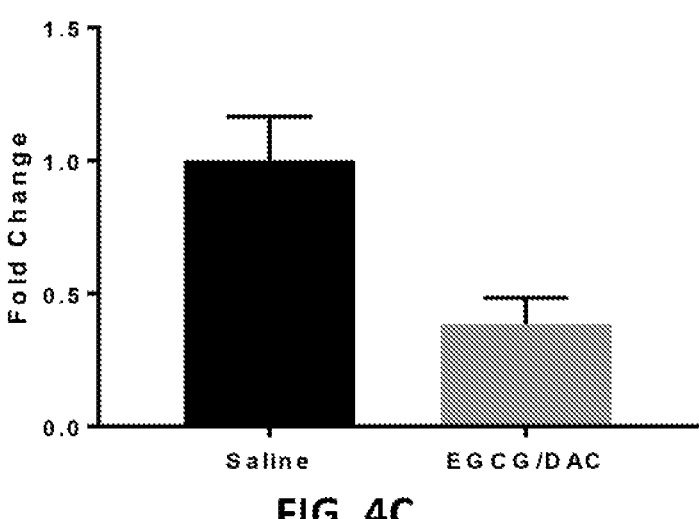
FIG. 4C illustrates Axin2 gene expression quantitated by qRT-PCR from the same tumors in 4A after EGCG/DAC treatment and saline treatment. * represents $p < 0.05$.

Western blot analysis for β-catenin expression in MDA-MB-231 tumors from 4 untreated mice and 4 EGCG/DAC treated mice. Tumors dissected from MDA-MB-231 human xenografts is shown in FIG. 4A. FIG. 4B illustrates a quantification graph combing data from three western blot each with 4 untreated and four treated samples. Actin was used as a loading control. As shown in FIG. 4C, Axin2 gene expression was tested by qRT-PCR after EGCG/DAC treatment and saline treatment. It was tested in 6 treated and 7 untreated tumors dissected from MDA-MB-231 human xenograft mice. * represents significant decrease in protein level after EGCG/DAC treatment. P<0.05. ** represents significant decrease in fold change after EGCG/DAC treatment; P<0.01. Data represented as mean±SEM.

Example 5—Immunohistochemistry of MHC-I

Figure 5A:
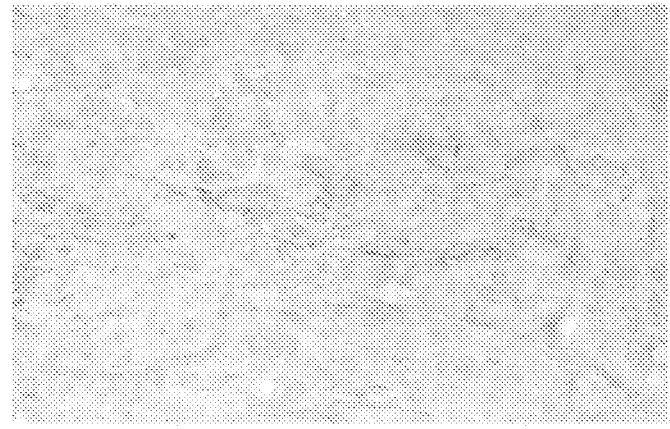
FIG. 5A-FIG. 5C illustrate the immunohistochemistry of MHC-I in a TNBC human xenograft (immune compromised) mouse model.
Figure 5B:
Figure 5C:
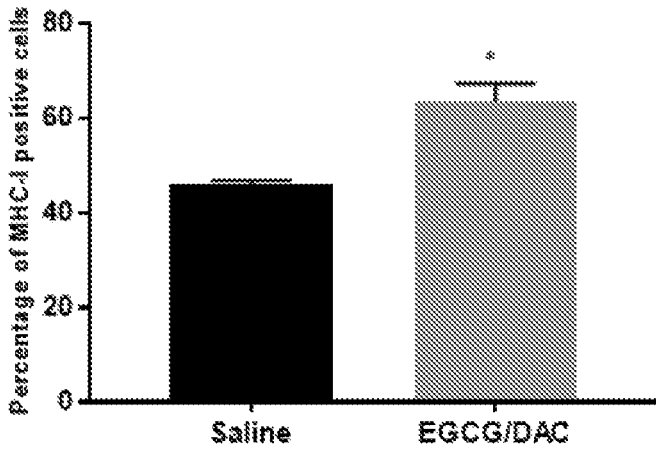

Different sections of tumors were stained with pan MHC-I antibody. Allred scoring system in scale 0 to 8 was used. Low level of MHC-I was observed in control group (Average Allred score=5) (as shown in FIG. 5A) while strong MHC-I expression was observed in EGCG/DAC treated group (Average Allred score=8) (FIG. 5B). FIG. 5C illustrates a quantification graph of the percentage of MHC-I positive cells in 4 control tumors and 4 EGCG/DAC treated tumors dissected from MDA-MB-231 human xenograft mice. * represents significant increase after EGCG/DAC treatment. P<0.01. Data represented as mean±SEM.

Example 6—Immunohistochemistry of MHC-II

Figure 6A:
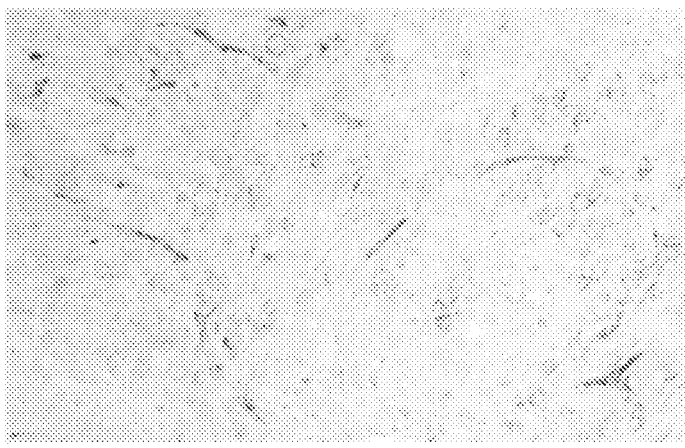
FIG. 6A-FIG. 6C illustrate the immunohistochemistry of MHC-II in a TNBC human xenograft (immune compromised) mouse model.
Figure 6B:
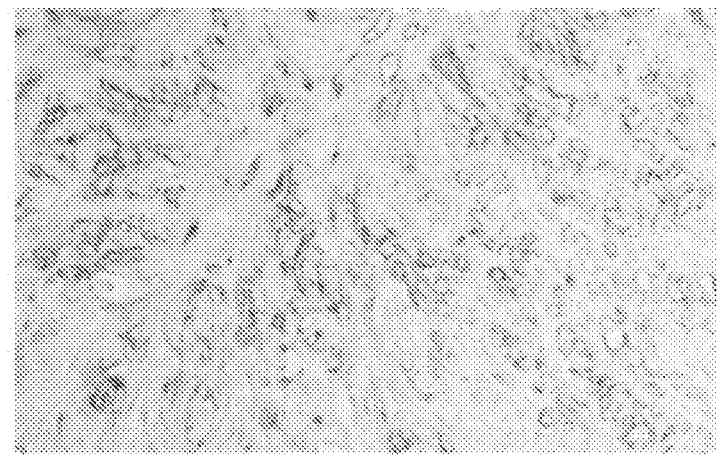
Figure 6C:
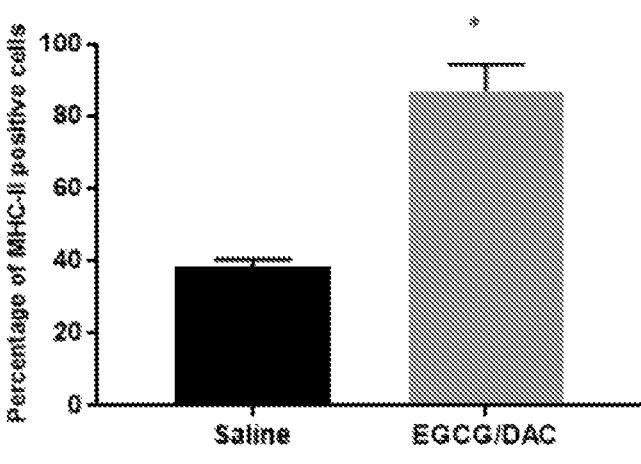

Different sections of tumors were stained with anti-MHC-II antibody. Allred scoring system in scale 0 to 8 was used. FIG. 6A illustrates the control group (Average Allred score=4). FIG. 6B illustrates the EGCG/DAC treated group (Average Allred score=8). FIG. 6C illustrates a quantification graph of the percentage of MHC-II positive cells in 4 control tumors and 4 treated groups. * represents significant increase after EGCG/DAC treatment. P<0.05. Data represented as mean±SEM.

Example 7—Fold Change in mRNA Level of Cancer Testis Antigen

Figure 7:
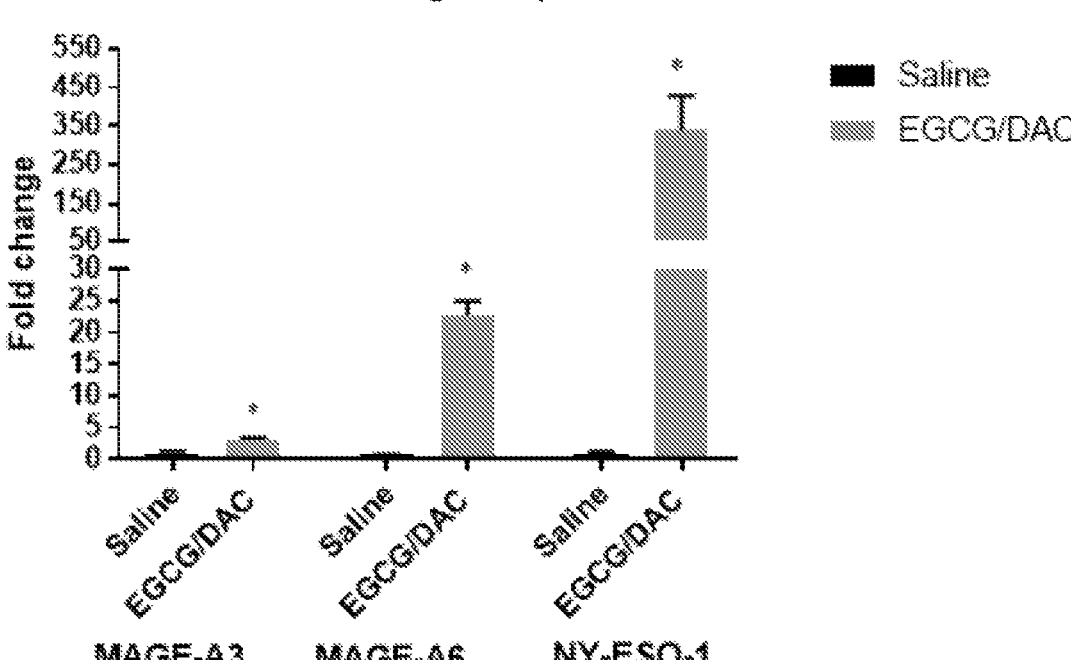
FIG. 7 illustrates that EGCG/DAC treatment increases immunogenicity in a TNBC human xenograft (immune compromised) mouse model by measuring the gene expression of Cancer Testis Antigens using qRT-PCR. * represents p<0.05.

As shown in FIG. 7, the gene expression of MAGE-A3, MAGE-A6 and NY-ESO-1 was tested by qRT-PCR in tumors treated with EGCG/DAC and in control group. It was tested in 5 treated and 5 untreated tumors. *P<0.005. Data represented as mean±SEM.

Example 8—Protein Expression for STAT3 Phosphorylation Status

Figure 8B:
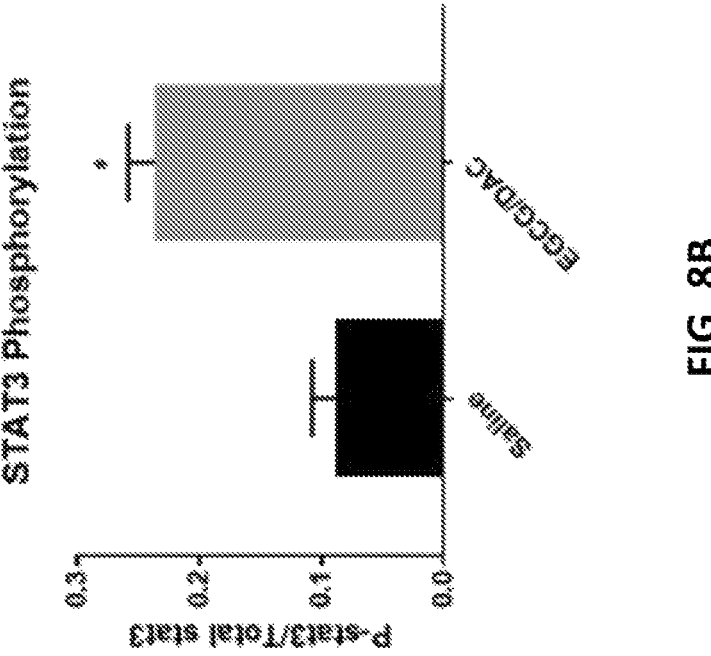
FIG. 8B illustrates a quantification graph of STAT3 phosphorylation combining data from three western blots each with 4 untreated and four treated samples; * represents p<0.05.
Figure 8A:
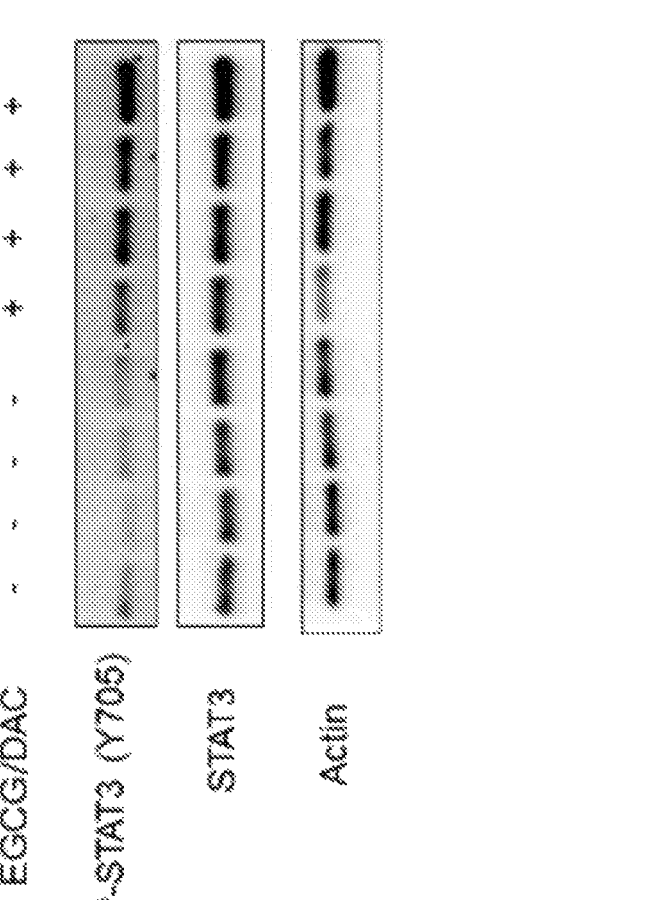
FIG. 8A illustrates a western blot of STAT3 phosphorylation at the JAK kinase site (Y705), total STAT3 protein, and internal control actin from tumors dissected from four control (−) and four EGCG/DAC treated (+) MDA-MB-231 human xenografts.

FIG. 8A illustrates a Western blot analysis for P-STAT3 in 4 untreated mice and 4 EGCG/DAC treated mice. FIG. 8B illustrates a quantification graph combing data from two western blot each with 4 untreated and 4 treated samples. Actin was used as a loading control. * represents significant increase in P-STAT3 level after EGCG/DAC treatment. P<0.005. Data represented as mean±SEM.

Figure 9A:
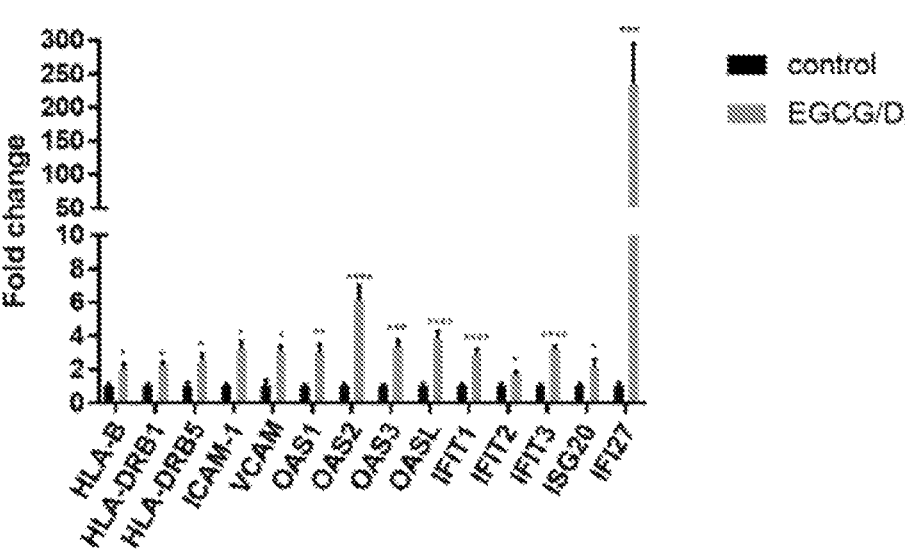
FIG. 9A illustrates the fold change in mRNA level determined by qRT-PCR for IFN stimulated genes (ISGs) in a TNBC human xenograft (immune compromised) mouse model, including MHC-I and MHC-II genes. * represents p<0.05,  represents p<0.01, * represents p<0.005
Figure 9B:
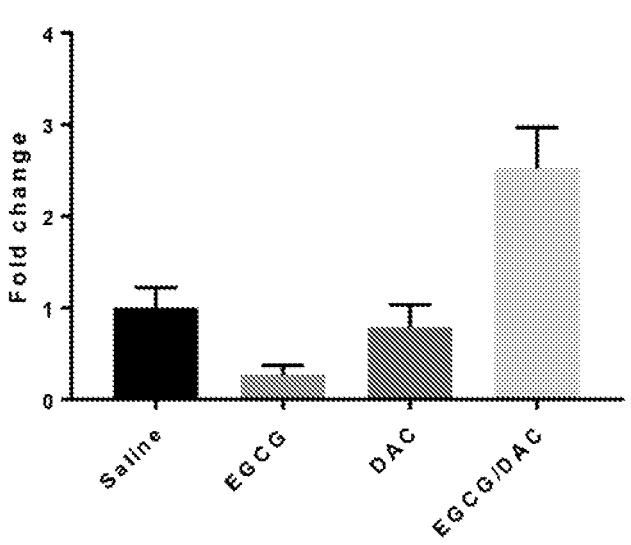
FIG. 9B illustrates the synergy of the compound combination for HLA-DRB5 expression measured using qRT-PCR. * represents p<0.05.

Example 9—Fold Change in mRNA Level for IFN Stimulated Genes (ISGs), Including MHC-I and MHC-II Genes As shown in FIG. 9A, the expression of each gene was tested by qRT-PCR after EGCG/DAC treatment and saline treatment. It was tested in 6 treated and 5 untreated tumors. *P<0.05, P<0.01, *P<0.005, **P<0.001. Data represented as mean±SEM. FIG. 9B** shows the effect of individual components of the combination (EGCG only or DAC only) have no significant effect on HLA-DRB5 (MHC II) gene expression. Only the combination of EGCG and DAC resulted n a significant increase in HLA-DRB5 gene expression. *P<0.05

Figures 10A, 10B:
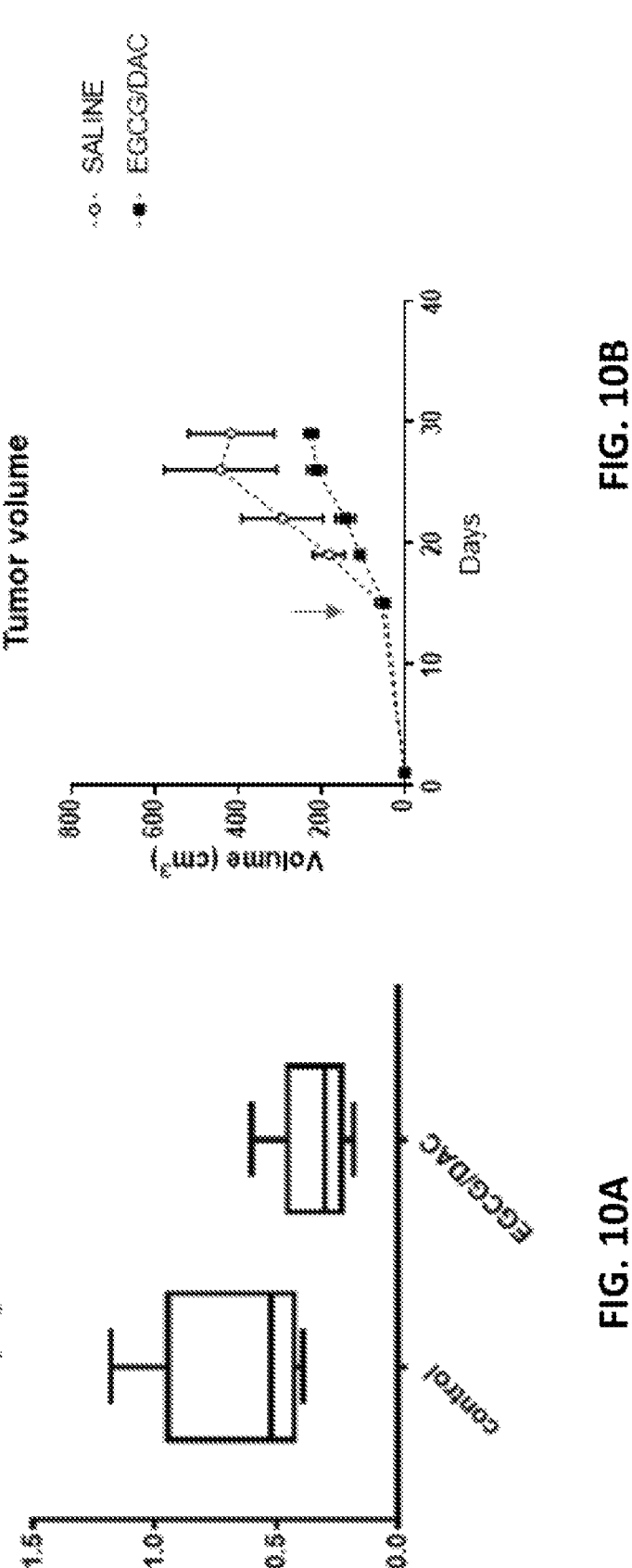
FIG. 10A illustrates the effect of EGCG/DAC on final tumor weight in a TNBC syngeneic (immune competent) mouse model (p<0.05).
FIG. 10B illustrates the effect of EGCG/DAC on tumor growth in a TNBC syngeneic (immune competent) mouse model. Arrow indicates beginning of treatment and * represents p<0.05.

Example 10—the Effect of EGCG/DAC in TNBC Syngeneic (Immune Competent) Mouse Model 4T1-12B (a specific subclone tagged with luciferase and originated from Balb/c mouse) was implanted orthotopically into Balb/c mice. At least 5 mice were treated with EGCG (16.5 mg/kg) and DAC (0.5 mg/kg) and 5 mice treated with saline for the indicated time. As shown in FIG. 10A, tumors weights were measured after 2 weeks of treatment. P=0.08. As shown in FIG. 10B, tumors volumes were measured with calipers for the indicated time. At two later times the difference in measured size was significant. *P<0.05

Example 11—Immunohistochemistry of Ki67 Proliferation Marker

Figure 11A:
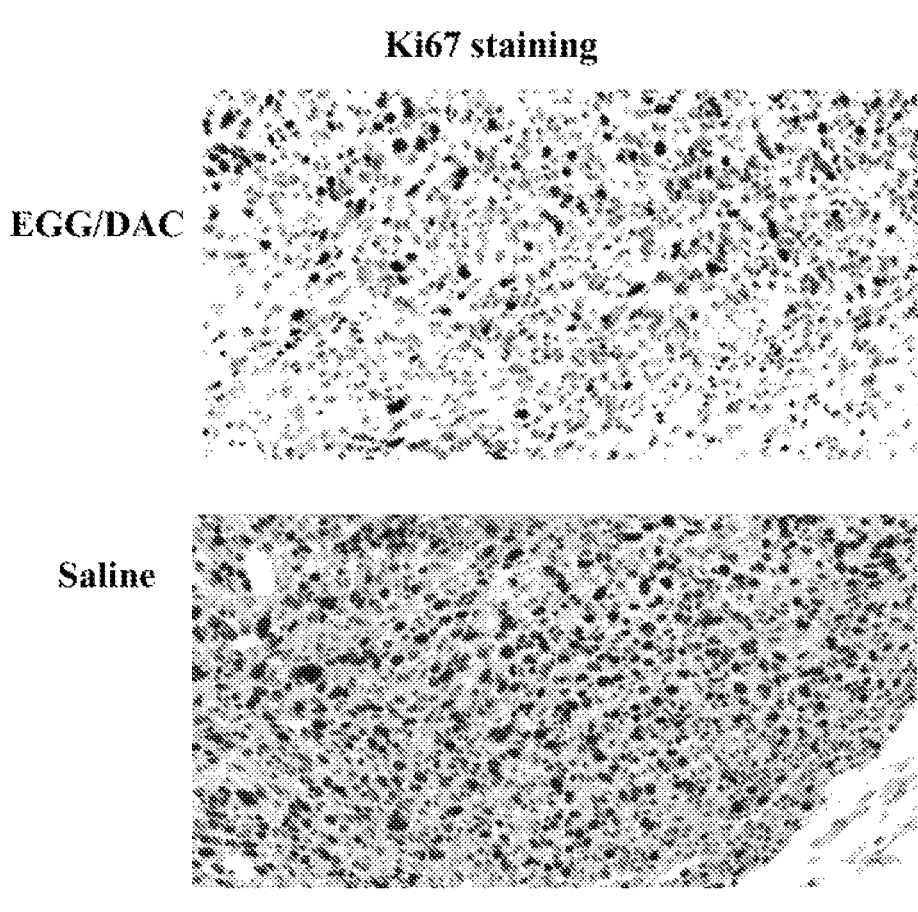
FIG. 11A-FIG. 11B illustrate the effect of EGCG/DAC on tumor growth in a 4T1 TNBC syngeneic (immune competent) mouse model by staining for the proliferation marker Ki67.
Figure 11B:
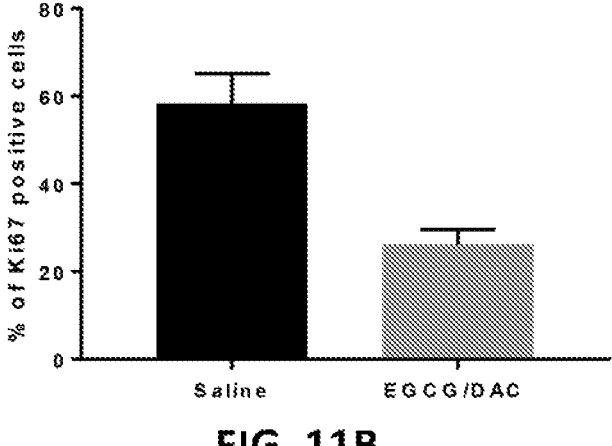

Different sections of tumors were stained with anti-Ki67 antibody. Allred scoring system in scale 0 to 8 was used. FIG. 11A illustrates the control group (Average Allred score=6) and the EGCG/DAC treated group (Average Allred score=3). FIG. 11B illustrates a quantification graph of the percentage of Ki67 positive cells in 4 control tumors and 4 treated groups. * represents significant increase after EGCG/DAC treatment. P<0.05. Data represented as mean±SEM.

Figure 12A:
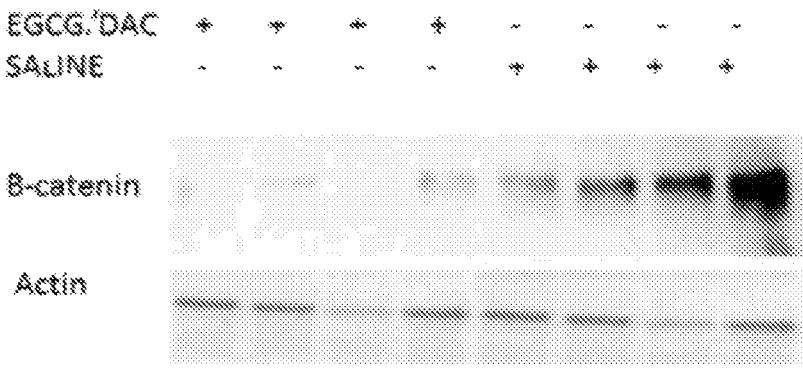
FIG. 12A illustrates a western blot of β-catenin and internal control actin from tumors dissected from control (−) and EGCG/DAC treated (+) 4T1 mouse TNBC syngeneic (immune competent) xenografts.
Figure 12B:
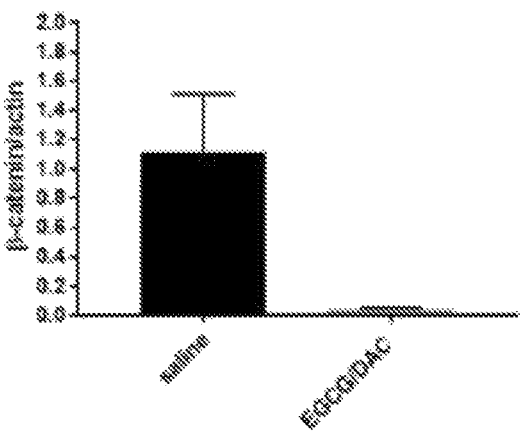
FIG. 12B illustrates a quantification graph combining data from three western blot each with 4 untreated and four treated samples.
Figure 12C:
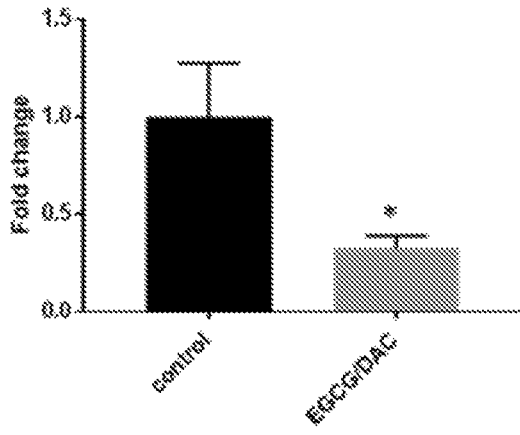
FIG. 12C illustrates Axin2 gene expression quantitated by qRT-PCR from the same tumors in 4A after EGCG/DAC treatment and saline treatment. * represents p<0.05.

Example 12—the Effect of EGCG/DAC on Wnt Signaling in TNBC Syngeneic (Immune Competent) Mouse Model FIG. 12A illustrates a Western blot analysis for β-catenin in 4 untreated mice and 4 EGCG/DAC treated mice. FIG. 12B illustrates a quantification graph combing data from two western blot each with 4 untreated and 4 treated samples. Actin was used as a loading control. As shown in FIG. 12C, Axin2 gene expression was tested by qRT-PCR after EGCG/DAC treatment and saline treatment. It was tested in 5 treated and 5 untreated tumors. * represents significant decrease after EGCG/DAC treatment. P<0.01. Data represented as mean±SEM.

Figure 13B:
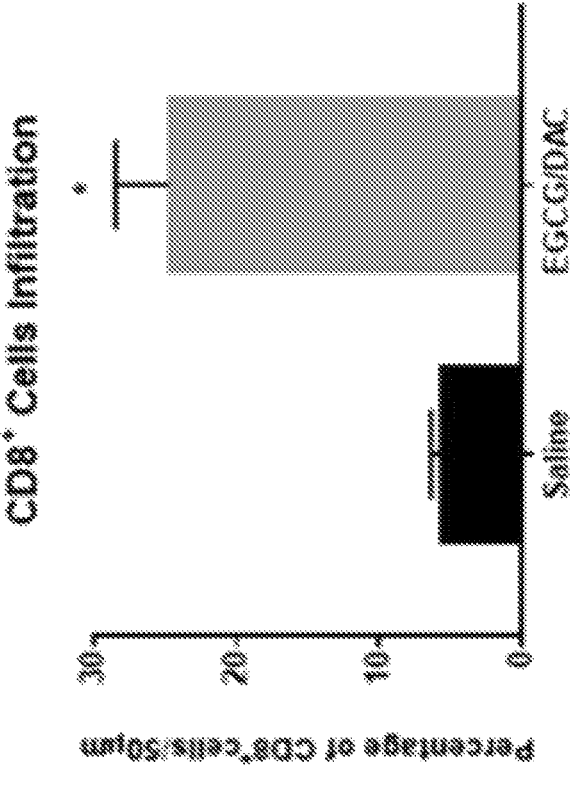
FIG. 13A-FIG. 13B illustrate the immunohistochemistry of CD8+ T-cells in a TNBC syngeneic (immune competent) mouse model.
Figure 13A:
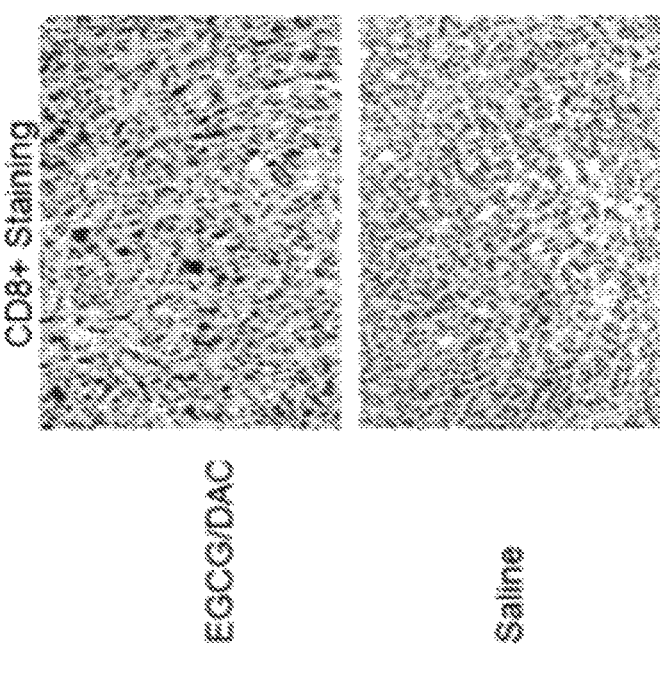

Example 13—Immunohistochemistry of CD8+ T-Cells in TNBC Syngeneic (Immune Competent) Mouse Model As shown in FIG. 13A, different sections of different treated and untreated tumors were stained with anti-CD8$^+$ antibody. Strong and dense CD8+ cells infiltration was observed in EGCG/DAC treated group. FIG. 13B illustrates a quantification graph of the percentage of CD8$^+$ cells in 5 control tumors and 5 treated tumors. * represents significant increase after EGCG/DAC treatment. P<0.001. Data represented as mean±SEM.

Figures 14A, 14B:
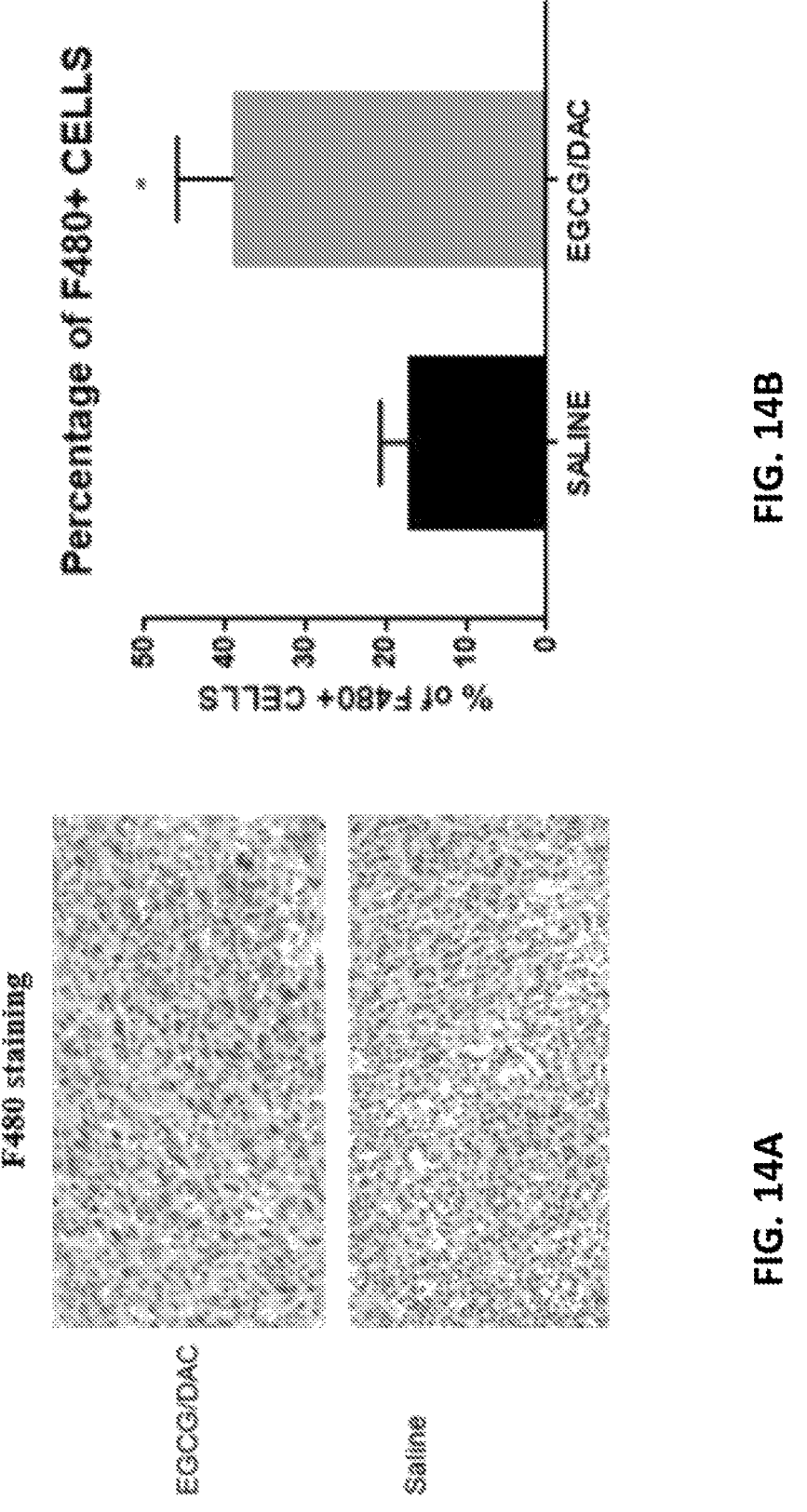
FIG. 14A-FIG. 14B illustrate the immunohistochemistry of macrophage marker F/480 positive cells in a TNBC syngeneic (immune competent) mouse model.

Example 14—Immunohistochemistry of F/480 Cells in TNBC Syngeneic (Immune Competent) Mouse Model As shown in FIG. 14A, different sections of different treated and untreated tumors were stained with anti-F/480 antibody. Increase in macrophage cells infiltration was observed in EGCG/DAC treated group. FIG. 14B illustrates a quantification graph of the percentage of F/480 positive cells in 5 control tumors and 5 treated tumors. * represents significant increase after EGCG/DAC treatment. P<0.05. Data represented as mean±SEM.

Figure 15:
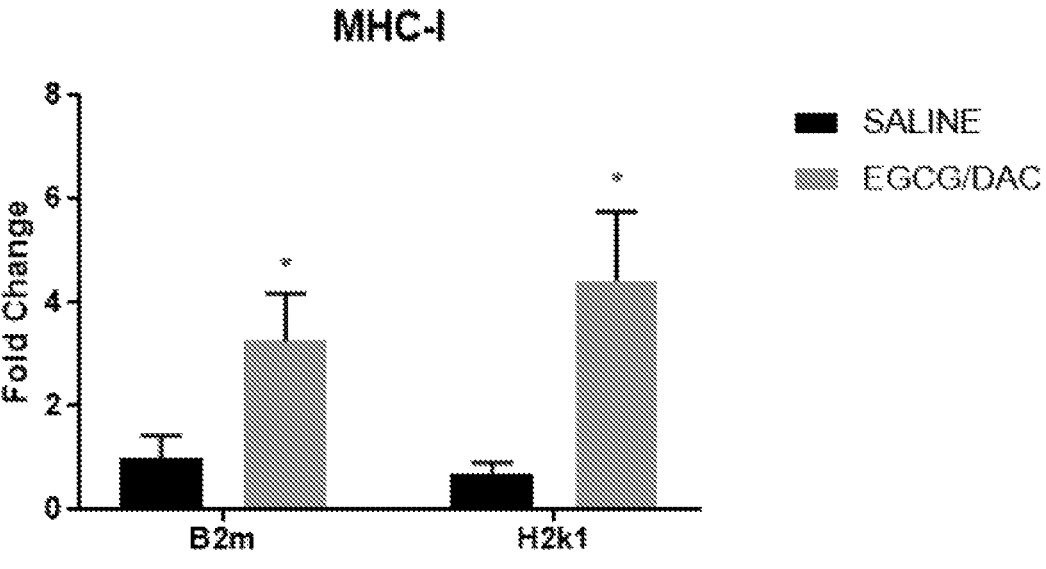
FIG. 15 illustrates a fold change in mRNA level for MHC-I genes B2m and H2k1in a TNBC syngeneic (immune competent) mouse model. * represents p<0.05.

Example 15—Fold Change in mRNA Level for MHC-I in TNBC Syngeneic Mouse (Immune Competent) Model As shown in FIG. 15, expression of B2m and H2k1 genes were tested by qRT-PCR after EGCG/DAC treatment and saline treatment. It was tested in 5 treated and 5 untreated tumors. * represents significant increase in fold change after EGCG/DAC treatment; P<0.05. Data represented as mean±SEM.

Figure 16:
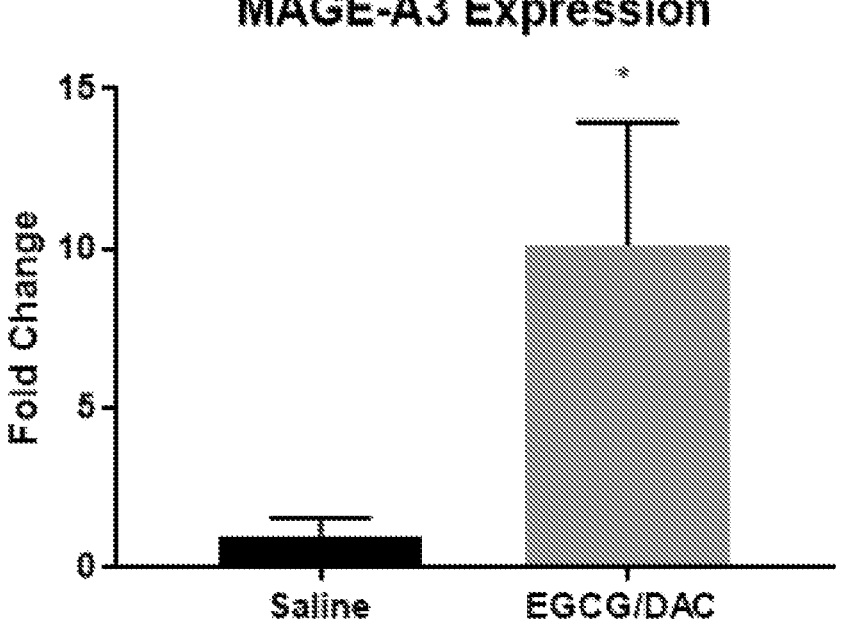
FIG. 16 illustrates the fold change in mRNA level from 4 individual control and 4 individual EGCG/DAC treated tumors of Cancer Testis Antigen MAGE-A3, determined by qRT-PCR, in a TNBC syngeneic (immune competent) mouse model. * represents p<0.05.

Example 16—Fold Change in mRNA Level of Cancer Testis Antigen in TNBC Syngeneic (Immune Competent) Mouse Model As shown in FIG. 16, the gene expression of MAGE-A3 was tested by qRT-PCR in tumors treated with EGCG/DAC and in control group. It was tested in treated and 5 untreated tumors. *P<0.05. Data represented as mean±SEM.

Figure 17A:
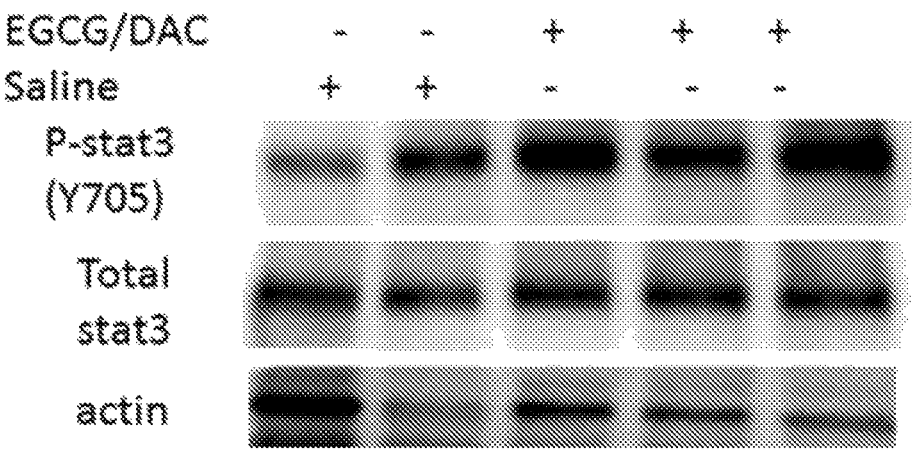
FIG. 17A illustrates a representative western blot of STAT3 phosphorylation at the JAK kinase site (Y705), total STAT3 protein, and internal control actin from tumors dissected from control and EGCG/DAC treated 4T1 TNBC mouse syngeneic (immune competent) xenografts.
Figure 17B:
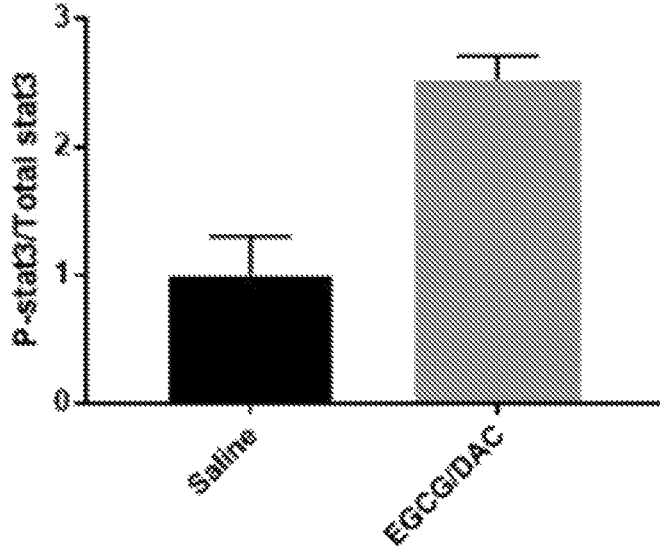
FIG. 17B illustrates a quantification graph of STAT3 phosphorylation combining data from three western blots each with 4 untreated and four treated samples; * represents p<0.05.

Example 17—Protein Expression for STAT3 Phosphorylation Status in TNBC Syngeneic (Immune Competent) Mouse Model FIG. 17A illustrates a Western blot analysis for P-STAT3 in untreated mice and EGCG/DAC treated mice. FIG. 17B illustrates a quantification graph combing data from two western blot each with 4 untreated and 4 treated samples. Actin was used as a loading control. * represents significant increase in P-STAT3 level after EGCG/DAC treatment. P<0.005. Data represented as mean±SEM.

Figure 18:
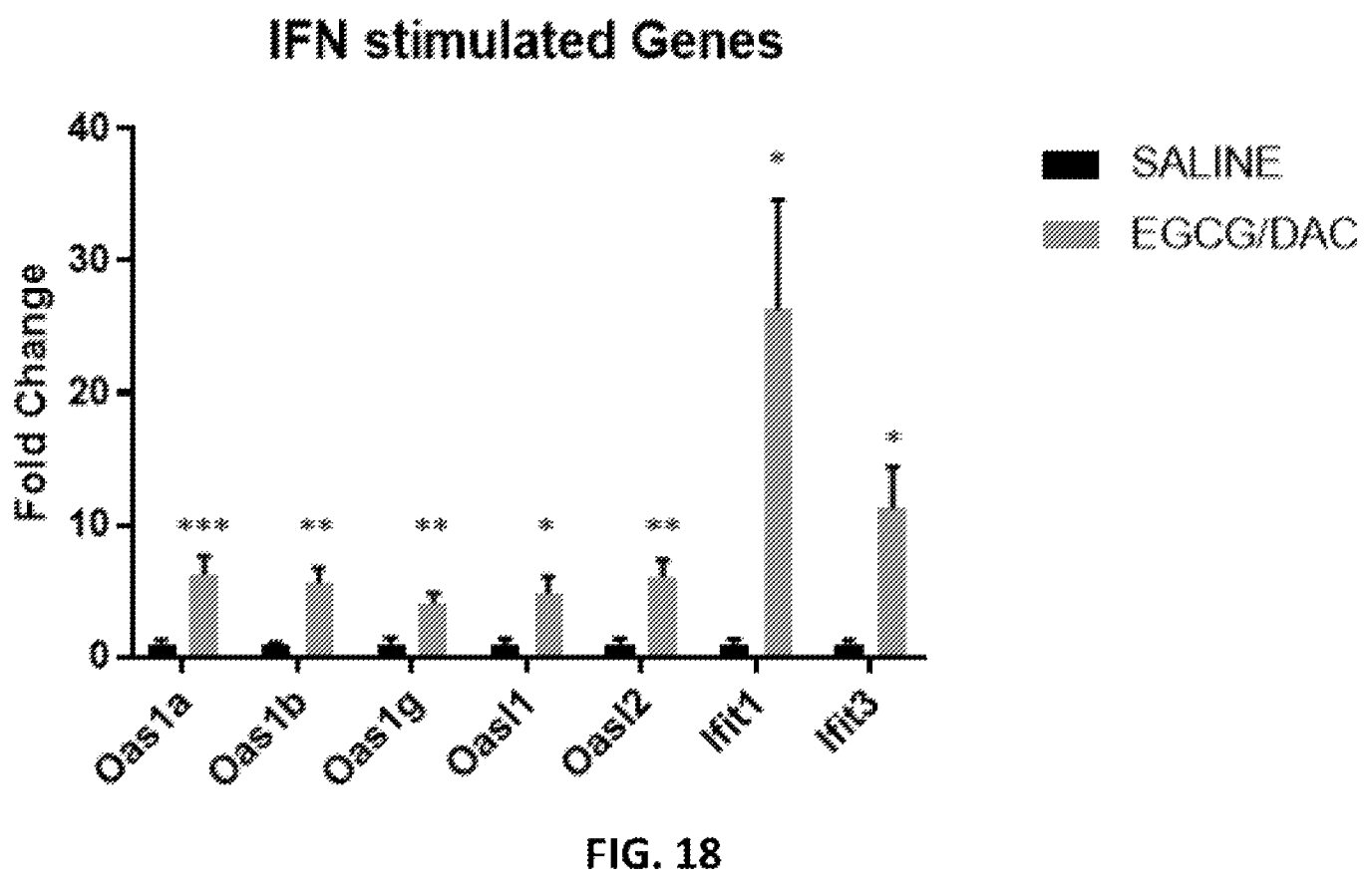

Example 18—Fold Change in mRNA Level for ISGs in TNBC Syngeneic (Immune Competent) Mouse Model As shown in FIG. 18, the expression of each gene was tested by qRT-PCR after EGCG/DAC treatment and saline treatment. It was tested in 6 treated and 6 untreated tumors. *P<0.05, P<0.01, *P<0.005. Data represented as mean±SEM.

Example 19—Fold Change in mRNA Level for PFR-1 after EGCG/DAC Treatment

Figure 19:
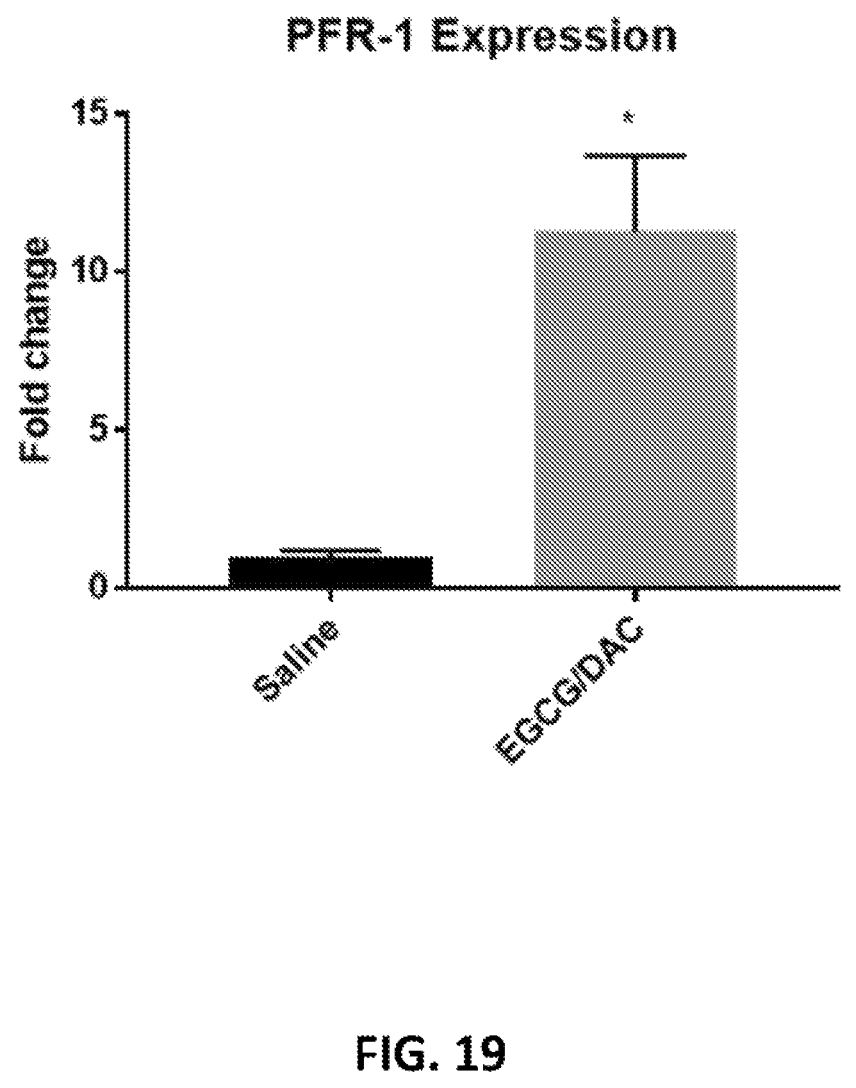

As shown in FIG. 19, PFR-1 gene expression was tested by qRT-PCR after EGCG/DAC treatment and saline treatment. It was tested in 6 treated and 7 untreated tumors. * represents significant increase in fold change after EGCG/DAC treatment; P<0.001. Data represents as mean±SEM.

Example 20—Correlation Between STAT3 Phosphorylation and ISGs Expression

To confirm the activation of IFNα/β and IFNγ pathways in the mice model after EGCG/DAC treatment, phosphorylation status of STAT3 (a key mediator of IFN signaling) was tested. Quantification of western blot (FIG. 17) shows that the tumor samples treated with EGCG/DAC had higher levels of phosphorylated STAT3 than the samples treated with saline. As shown in FIG. 20, STAT3 phosphorylation status was positively correlated with mRNA levels of OAS2, OAS3, and OASL in EGCG/DAC treated tumors (FIG. 18). $R^2$ value was calculated using GraphPad Prism 7.0.

Figures 21A, 21B:
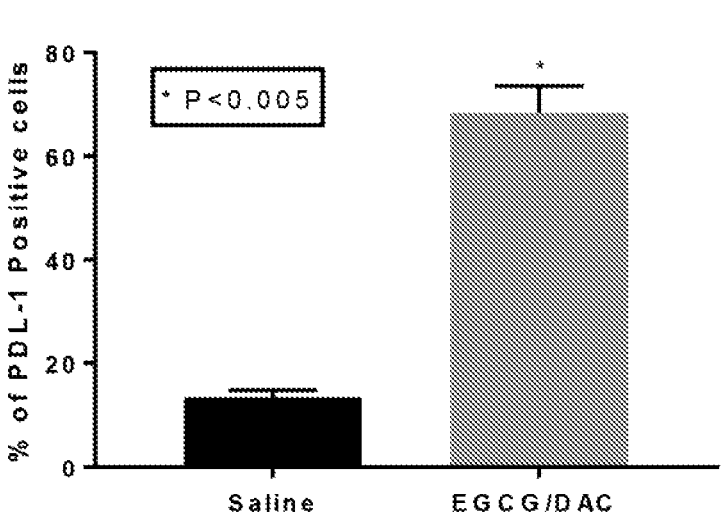
FIG. 21A-FIG. 21C illustrate the immunohistochemistry of macrophage marker PDL-1 positive cells in a TNBC syngeneic (immune competent) mouse model.
Figure 21C:
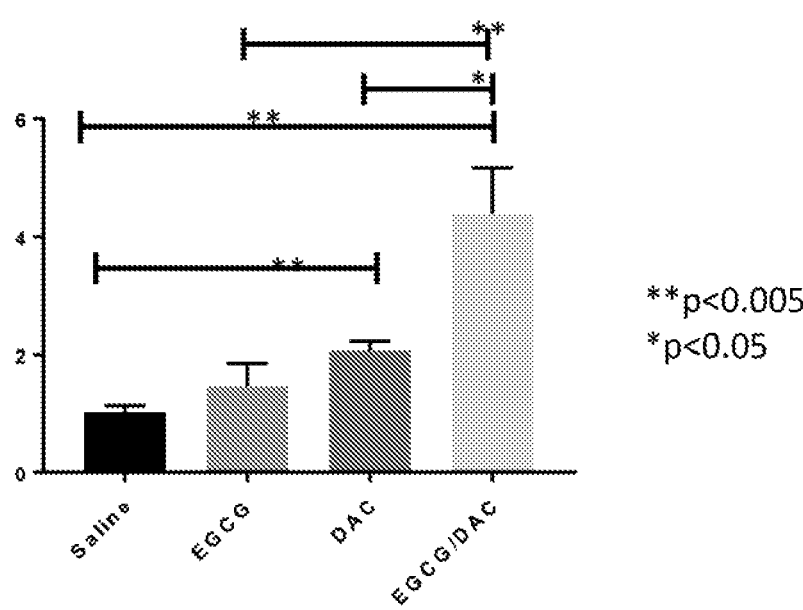

Example 21—Immunohistochemistry of PDL-1 in TNBC Syngeneic (Immune Competent) Mouse Model and PDL-1 Expression in Human TNBC Xenograft (Immune Compromised) Mouse Model As shown in FIG. 21A, different sections of different treated and untreated tumors were stained with anti-PDL-1 antibody. Strong and dense PDL-1 cells were observed in EGCG/DAC treated group. FIG. 21B illustrates a quantification graph of the percentage of PDL-1 cells in 5 control tumors and 5 treated tumors. * represents significant increase after EGCG/DAC treatment. P<0.001 FIG. 21C shows the relative gene expression of PDL-1 in human tumors in immune compromised mice from EGCG only, DAC only and EGCG plus DAC combined treatment groups (4-5 mice each group). DAC only was a significant 2-fold increase while the combination was greater than 4-fold increase and highly significant. * represents significant increase (P<0.05). ** represents highly significant increase (P<0.005). Data represented as mean±SEM.

Figures 22A, 22B:
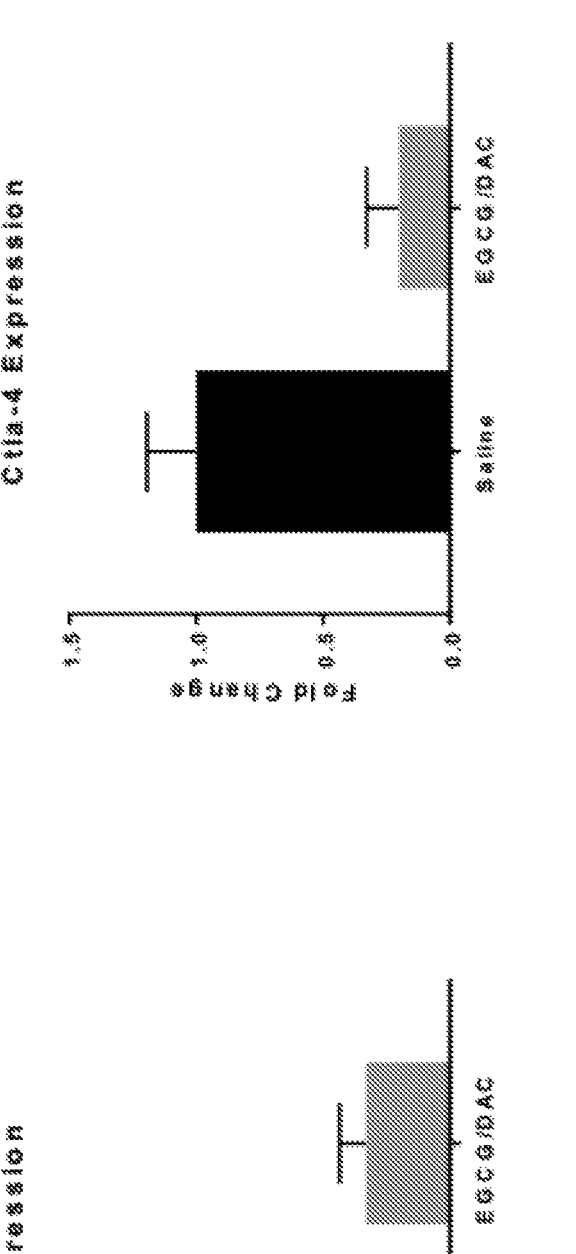
FIG. 22A illustrates the fold change in mRNA level from 4 individual control and 4 individual EGCG/DAC treated tumors of PD-1, determined by qRT-PCR, in a TNBC syngeneic (immune competent) mouse model. * represents p<0.05.
FIG. 22B illustrates the fold change in mRNA level from 4 individual control and 4 individual EGCG/DAC treated tumors of CTLA-4, determined by qRT-PCR, in a TNBC syngeneic (immune competent) mouse model. * represents p<0.05.

Example 22—Both PD-1 and CTLA-4 Expression are Inhibited by Treatment with EGCG/DAC in a Syngeneic Mouse Model of TNBC As shown in FIG. 22A illustrates the fold change in mRNA level from 4 individual control and 4 individual EGCG/DAC treated tumors of PD-1, determined by qRT-PCR, in a TNBC syngeneic (immune competent) mouse model. * represents p<0.05. FIG. 22B illustrates the fold change in mRNA level from 4 individual control and 4 individual EGCG/DAC treated tumors of CTLA-4, determined by qRT-PCR, in a TNBC syngeneic (immune competent) mouse model. * represents p<0.05.

Figure 23A:
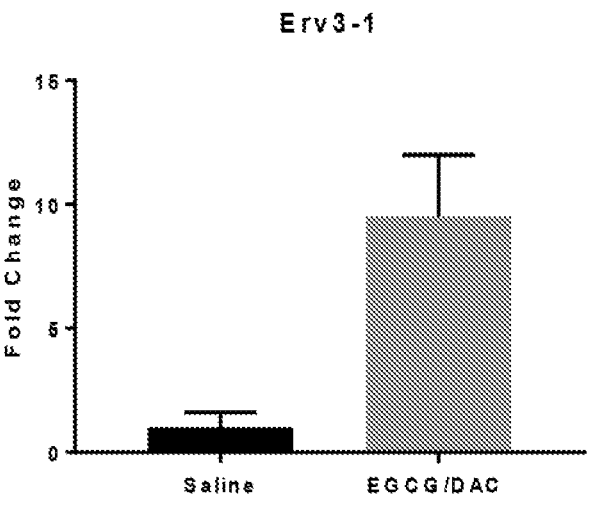
FIG. 23A-FIG. 23B illustrate that EGCG/DAC induces viral mimicry in a Syngeneic Mouse Model of TNBC.
Figure 23B:
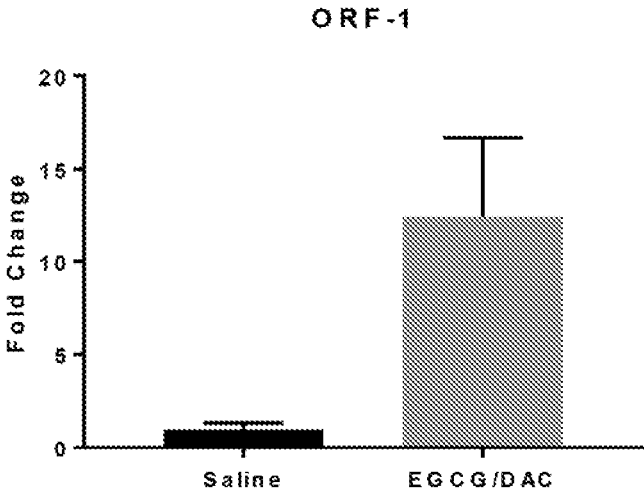

Example 23—Fold Change in mRNA Level for Endogenous Retrovirus and LINE in TNBC Syngeneic Mouse (Immune Competent) Model As shown in FIG. 23A and FIG. 23B, expression of endogenous retrovirus Erv3-1 and LINE-1 (ORF-1) genes were tested by qRT-PCR after EGCG/DAC treatment and saline treatment (5 treated and 5 untreated tumors). * represents significant increase in fold change after EGCG/DAC treatment; $P<0.05$. Data represented as mean±SEM.

Example 24—Protein Expression for STAT3 Phosphorylation Status

Figures 24A, 24B:
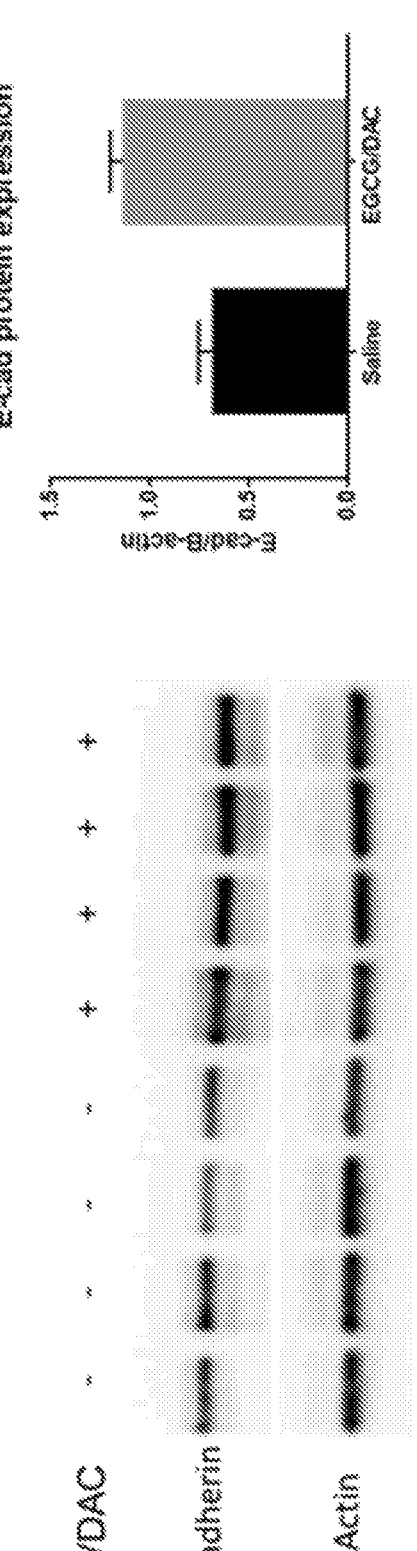
FIG. 24A-FIG. 24B illustrates the effect of EGCG/DAC on E-cadherin protein expression in TNBC syngeneic mouse model.

FIG. 24A illustrates a Western blot analysis for E-Cadherin in 4 untreated mice and 4 EGCG/DAC treated mice. FIG. 24B illustrates a quantification graph combing data from two western blot each with 4 untreated and 4 treated samples. Actin was used as a loading control. * represents significant increase in P-STAT3 level after EGCG/DAC treatment. $P<0.05$. Data represented as mean±SEM.

Example 25—Proposed Mechanism of the Combination of EGCG and DAC

Figure 25:
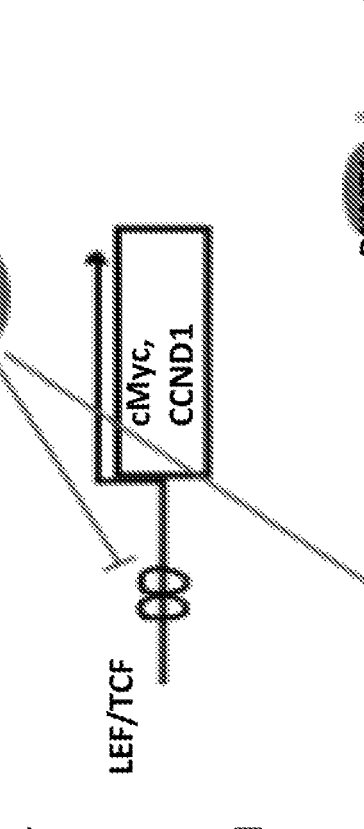
FIG. 25 illustrates the direct actions and mechanisms of the EGCG/DAC combination. Specifically, published data demonstrates that EGCG stabilizes HBP1 mRNA, suppresses Wnt signaling and inhibits DNMT1 expression. Decitabine (DAC) is an FDA-approved chemotherapeutic and is a competitive inhibitor of DNMT1. The combination of EGCG and DAC together is therefore predicted to act additively or possibly synergistically to activate Wnt inhibitor sFRP1 gene expression, thus boosting the individual compounds efficacy to inhibit Wnt signaling by activating both HBP1 and sFRP1 expression.

FIG. 25 illustrates the summary of work on the molecular regulation of Wnt signaling via Wnt inhibitors HBP1, EGCG and target genes including DNMT1 and sFRP1. By choosing compounds to activate one Wnt inhibitor (HBP1-EGCG) and to inhibit the HBP1 target DNMT1 secondarily with decitabine (DAC) a second Wnt inhibitor (sFRP1) was expected to be induced, resulting in amplified Wnt signaling inhibition.

Example 26—Summary of Proposed Outcomes of the Effects EGCG and DAC Combination on Tumor-Immune System Interactions FIG. 26 summarises of the outcomes of the EGCG/DAC combination (CHA1) in altering the fate of the tumor by: 1) Altering important signaling pathways such as Wnt, 2) reprograming the tumor to increase antigen presentation in immune cell infiltration and 3), changing the tumor from immunologically "cold" to having immunologically "hot" characteristics.

Figure 27:
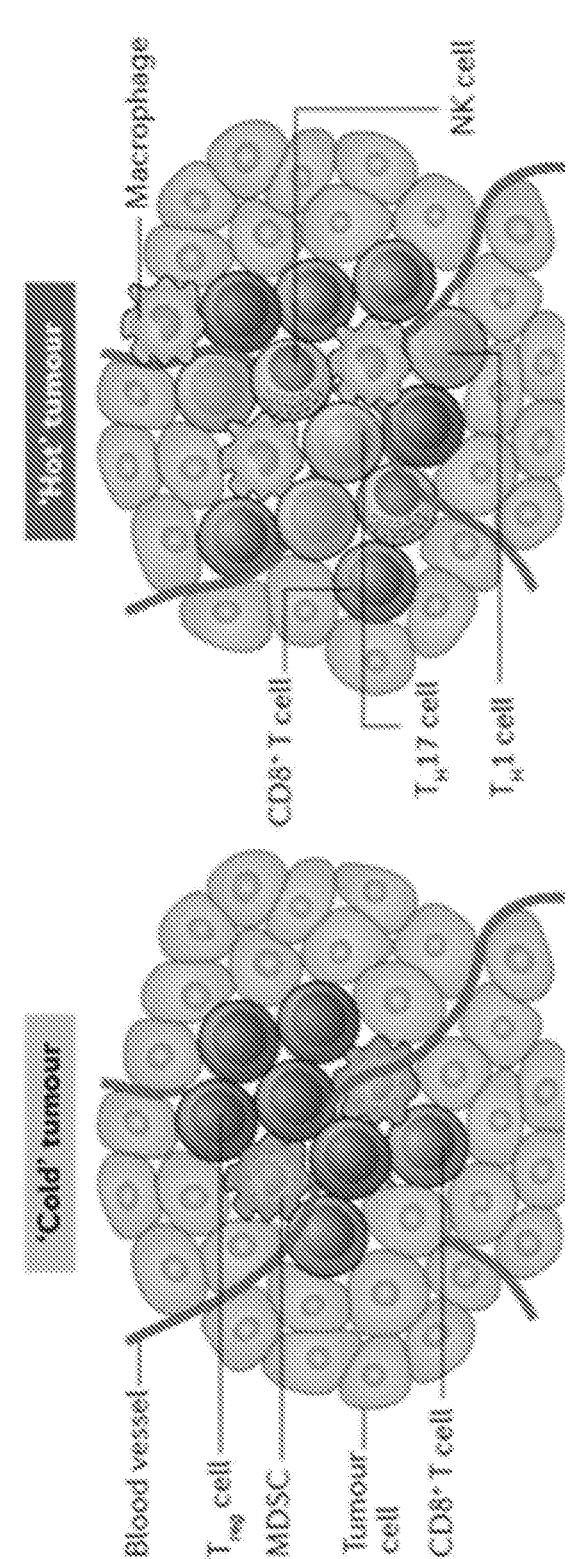
FIG. 27 illustrates the detailed output of ECGC/DAC treatment on the biological and immunological characteristics of tumor cells. Specifically the tumor is reprogrammed by treatment to change from a "cold" tumor that has evaded the immune system, to become a "hot" tumor that is infiltrated with active immune cells. The "hot" tumor characteristic is a required prerequisite for efficacy of immunotherapy in numerous clinical and FDA-approved protocols.

Example 27—Details the Output of ECGC/DAC Treatment on the Biological and Immunological Characteristics of Tumor Cells FIG. 27 illustrates how EGCG/DAC combination dramatically re-programs tumors in multiple ways, resulting in the hallmarks of increased visibility to the immune system. This reprogramming altered both the biological and immunological characteristics of the tumor, revealing a platform for analysis of any compound that can act in the same manner. 1. Wnt signaling is inhibited. 2. Mesenchymal character of the tumor is re-programed back to a epithelial-like state. 3. Expression of endogenous retroviruses are actived. 4. The viral mimicry response is induced. 5. Interferon-like JAK/STAT signaling is induced. 6. An interferon-stimulated gene signature is elicited, including increased expression of MHC proteins and PDL1. 7. Cancer Testis Antigens are rexpressed, a signature of increased immunogenicity. 8. Increased immunogenicity is observed, including tumor infiltration of T-cells and macrophage

Example 28—Technical Platform Summary for Discovering Compounds Such as EGCG and DAC Combination that Reprogram Tumors to Promote Tumor-Immune System Interactions FIG. 28 summarizes how the mechanisms defined in Examples 26 and 27 for EGCG/DAC combination are fully applicable as a general test for identifying other compounds that may also re-program tumors for increased immune sensitivity.

Figure 29C:
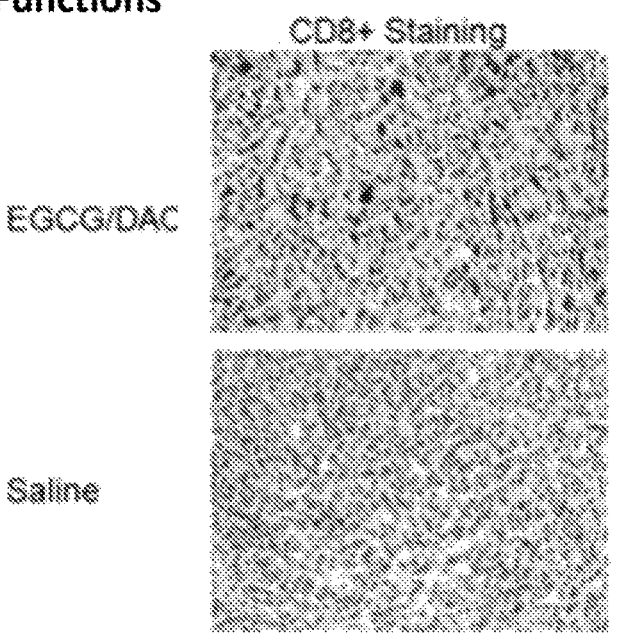
FIG. 29C illustrates sample experimental analyses of compound functions.
Figure 29D:
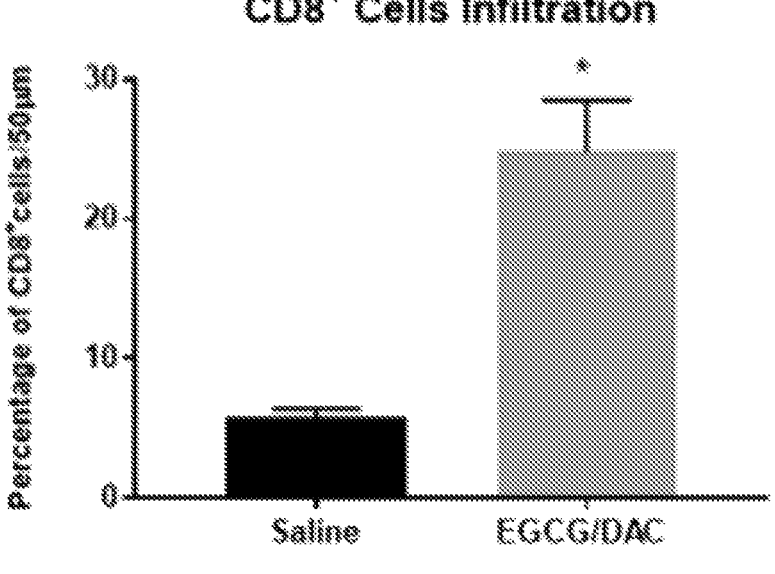
FIG. 29D illustrates sample experimental analyses of compound functions.

Example 29—Details of the Technical Platform Scientific Criteria for Discovering Compounds Such as EGCG and DAC Combination that Reprogram Tumors to Promote Tumor-Immune System Interactions FIG. 29A details the Cha Therapeutics scientific and technical platform for evaluating candidate compounds that function in a manner similar to EGCG/DAC. The specific criteria are: 1) inhibition of Wnt signaling, 2) alteration of epithelial-mesenchymal transitions, 3) re-expression of endogenous retrovirus expression, 4) activation of viral mimicry mechanisms, 5) activation of JAK/STAT signaling, 6) activation of an interferon stimulated gene signature (e.g. PDL-1, MI-ICs, etc), 7) re-expression of selected cancer testis antigens (CTAs) and 8) increased tumor immune cell infiltration (e.g. $CD8^+$ T-cells). FIGS. 29B-29D illustrate sample experimental analyses of compound functions.

Example 30—Trial Scheme of the Combination Therapy

Figure 30:
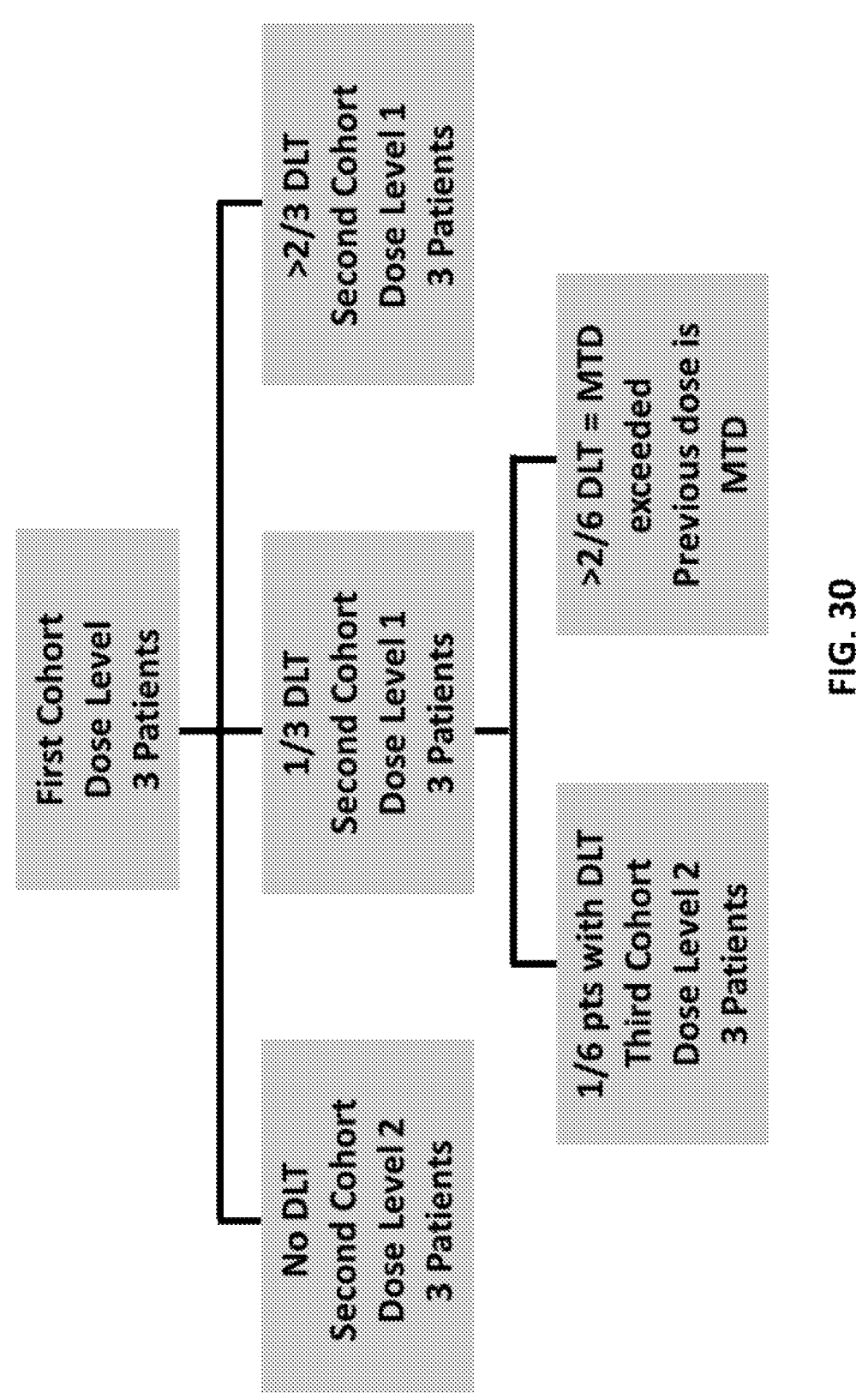
FIG. 30 illustrates the plan of a trial scheme for the evaluation of the combination.

This will be a non-randomized, dose-escalation study to evaluate the Maximum Tolerated dose (MTD), dose-limiting toxicities (DLTs), pharmacokinetics (PK), and pharmacodynamic (PD) profiles of increasing doses of orally administered EGCG in combination with IV-infused Decitabine (DAC) in subjects with malignancies that have failed to respond to standard therapy. 28-day cycles will be used. All levels will use 15 mg/m2 Decitabine DAC infused IV for 5 days and the indicated levels of oral EGCG tablets (Teavigo 94% 141 mg/tablet). Dose level-1=800 mg EGCG; Level 1=1200 mg EGCG; Level 2=1600 mg EGCG. The plan of the trial scheme is illustrated in FIG. 30.

Example 31—Trial Plan of the Combination Therapy

Four cycles of EGCG/DAC will be used. Gadolinium enhanced MRI or other imaging will be used, e.g., in cycle 0, 2, and/or 4. Standard blood draws and CSF draws will be performed.

Maximum tolerance dose will be evaluated. Assessment of dose limiting toxicities, assessment of PK and PD in blood and CSF, assessment of liver function and any adverse events 4.0 (NCI CTCAE) will be performed.

Effect of the combination therapy on CTC will be assessed. Axin-2 skin biopsy and gene expression analysis for responders and non-responders will be performed. Time to progression, CR or PR, increase in progression-free survival, time to treatment failure, and/or increased overall survival will be assessed.

Example 31—Patient Criteria

Patients who will benefit the most from the combination therapy may include, without limitation: those with histologically confirmed ER-PR- and Her2 negative; those having brain and other metastases>5 mm in longest dimension; those having no treatment within 28 days of the combination therapy, including radiation; those having no concurrent therapies; those having absolute neutrophil count>15000; those having Platelet Count>100,000/mm³; those having Creatinine<1.5 mg/dl; those having calculated clearance of Creatinine>45 ml/min; those having normal liver function; and those satisfying more than one of the criteria.

What is claimed is:

1. A method of stimulating a subject's immune system against cancer cells or treating a subject having cancer, the method consists of administering to the subject Agent (1) epigallocatechin gallate (EGCG), epigallocatechin (EGC), epicatechin gallate (ECG), epicatechin (EC), gallocatechin gallate (GCG), gallocatechin (GC), catechin gallate (CG), or catechin, or an ester, polyester, mono-glyceride, di-glyceride, tri-glyceride, pharmaceutically acceptable salt, glycoside, or metabolite thereof, Agent (2) a nucleoside analogue, and Agent (3) a checkpoint inhibitor, wherein a weight ratio of Agent (1) to Agent (2) is from about 25:1 to about 40:1;

wherein the metabolite of epigallocatechin gallate (EGCG), epigallocatechin (EGC), epicatechin gallate (ECG), epicatechin (EC), gallocatechin gallate (GCG), gallocatechin (GC), catechin gallate (CG), or catechin is selected from the group consisting of 3'-O-methyl EGC; 4'-O-methyl EGC; 3'-O-methyl EC; 4'-O-methyl EC; 1-(3',4',5'-trihydroxyphenyl)-3-(2'',4'',6''-trihydroxyphenyl)propan-2-ol; and
1-(3',5'-dihydroxyphenyl)-3-(2'',4'',6''-trihydroxyphenyl)propan-2-ol.

2. The method of claim 1, wherein the nucleoside analogue is a deoxycytidine analogue, deoxyuridine analogue, or a thymidine or deoxythymidine analogue.

3. The method of claim 1, wherein the Agent (1) is an epigallocatechin ester or an epicatechin ester.

4. The method of claim 1, wherein the Agent (1) is epigallocatechin gallate (EGCG) or epicatechin gallate (ECG).

5. The method of claim 1, wherein the cancer has origins or metastases in breast, bone, lung, liver, brain, stomach, intestine, colorectal, prostate, ovarian, uterine, cervical, kidney, spine, smooth muscle, skeletal muscle, or blood.

6. The method of claim 1, wherein the stimulating the subject's immune system comprises reduction of Wnt signaling and proliferation.

7. The method of claim 1, wherein the stimulating the subject's immune system comprises attenuation of a Warburg-like metabolism, activating antigen expression or presentation, augmenting JAK/STAT signaling, or activating IFN signaling.

8. The method of claim 1, wherein the checkpoint inhibitor is a PD-1 inhibitor, a PD-L1 inhibitor, or a CTLA-4 inhibitor.

9. The method of claim 1, wherein the Agent (1) or the Agent (2), or both are administered orally, topically, parenterally, or by inhalation.

10. The method of claim 1, wherein the Agent (2) is decitabine, and the Agent (1) is epigallocatechin gallate (EGCG).

11. The method of claim 1, wherein the cancer is a triple negative breast cancer.

12. The method of claim 1, wherein the cancer is a hematological cancer.

13. The method of claim 1, wherein the Agent (1) is epigallocatechin gallate (EGCG), or an ester, polyester, mono-glyceride, di-glyceride, tri-glyceride, pharmaceutically acceptable salt, or glycoside thereof.

14. The method of claim 1, wherein the Agent (1) is epigallocatechin gallate (EGCG) or a pharmaceutically acceptable salt thereof.

15. The method of claim 1, wherein the Agent (1) is epigallocatechin gallate (EGCG).

16. The method of claim 1, wherein the Agent (2) is decitabine or a pharmaceutically acceptable salt thereof.

17. The method of claim 1, wherein the Agent (2) is decitabine.

18. The method of claim 1, wherein the weight ratio of Agent (1) to Agent (2) is from about 30:1 to about 40:1.

19. The method of claim 1, wherein the weight ratio of Agent (1) to Agent (2) is from about 25:1 to about 35:1.

20. The method of claim 10, wherein the weight ratio of Agent (1) to Agent (2) is about 33:1.

* * * * *